United States Patent
Martin et al.

(10) Patent No.: US 10,743,777 B2
(45) Date of Patent: Aug. 18, 2020

(54) CARDIOVASCULAR PARAMETER ESTIMATION IN THE PRESENCE OF MOTION

(71) Applicant: QUALCOMM Incorporated, San Diego, CA (US)

(72) Inventors: Russel Martin, Menlo Park, CA (US); Shashank Narayanan, Sunnyvale, CA (US); Hithesh Reddivari, Sunnyvale, CA (US); Vidyut Naware, Sunnyvale, CA (US); Igor Tchertkov, San Jose, CA (US); Joseph Czompo, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 329 days.

(21) Appl. No.: 15/457,702

(22) Filed: Mar. 13, 2017

(65) Prior Publication Data

US 2018/0160912 A1    Jun. 14, 2018

Related U.S. Application Data

(60) Provisional application No. 62/431,759, filed on Dec. 8, 2016.

(51) Int. Cl.
*A61B 5/00* (2006.01)
*A61B 5/0205* (2006.01)
(Continued)

(52) U.S. Cl.
CPC ............ *A61B 5/0205* (2013.01); *A61B 5/024* (2013.01); *A61B 5/1123* (2013.01);
(Continued)

(58) Field of Classification Search
CPC ..... A61B 5/0205; A61B 5/024; A61B 5/1123; A61B 5/1118
See application file for complete search history.

(56) References Cited

U.S. PATENT DOCUMENTS

| 6,095,984 A | * | 8/2000 | Amano | .............. A61B 5/02438 |
| | | | | 600/481 |
| 2009/0187392 A1 | * | 7/2009 | Riskey | .................. A61B 5/1118 |
| | | | | 703/11 |

(Continued)

FOREIGN PATENT DOCUMENTS

| EP | 1908402 A1 | 4/2008 |
| EP | 22298813 A1 | 9/2010 |

(Continued)

OTHER PUBLICATIONS

Schäck T., et al., "A New Method for Heart Rate Monitoring During Physical Exercise Using Photoplethysmographic Signals", IEEE, 23rd European Signal Processing Conference (EUSIPCO), 2015, pp. 2716-2720.

(Continued)

*Primary Examiner* — Sean P Dougherty
*Assistant Examiner* — David Joseph Fernandez-Fidalgo
(74) *Attorney, Agent, or Firm* — Paradice and Li LLP

(57) ABSTRACT

Disclosed embodiments pertain to cardiovascular parameter (e.g. heart rate) measurements when motion is present. Biometric sensor signal measurements may be obtained based on cardiovascular parameters of a user; and motion sensor signal measurements may be obtained based on user motion. An activity type may be determined based on the motion sensor signals. For example, when non-motion related frequencies in a frequency domain representation of the biometric sensor signal are obscured by user motion, an activity type may be determined based on the motion sensor signals. Further, based on the activity type, for each cardio- (Continued)

vascular parameter (e.g. heart rate), a corresponding likely cardiovascular parameter value (e.g. a likely heart rate) may be determined. A corresponding fundamental frequency associated with the biometric sensor signal may then be determined for each cardiovascular parameter based on the motion sensor signal measurements and the corresponding likely cardiovascular parameter value.

28 Claims, 9 Drawing Sheets

(51) Int. Cl.
    *A61B 5/024*     (2006.01)
    *G16H 50/50*     (2018.01)
    *G16H 40/63*     (2018.01)
    *A61B 5/11*     (2006.01)
    *A61B 5/021*     (2006.01)
    *A61B 5/0295*     (2006.01)
    *A61B 5/145*     (2006.01)

(52) U.S. Cl.
    CPC .......... *A61B 5/1128* (2013.01); *A61B 5/6803* (2013.01); *A61B 5/7475* (2013.01); *G16H 40/63* (2018.01); *G16H 50/50* (2018.01); *A61B 5/0024* (2013.01); *A61B 5/0075* (2013.01); *A61B 5/021* (2013.01); *A61B 5/0295* (2013.01); *A61B 5/02444* (2013.01); *A61B 5/1118* (2013.01); *A61B 5/14542* (2013.01); *A61B 5/721* (2013.01); *A61B 5/7207* (2013.01); *A61B 5/7221* (2013.01); *A61B 5/7257* (2013.01); *A61B 5/7264* (2013.01)

(56) References Cited

U.S. PATENT DOCUMENTS

| | | |
|---|---|---|
| 2012/0022384 A1 | 1/2012 | Teixeira |
| 2012/0116183 A1 | 5/2012 | Osorio |
| 2012/0254100 A1* | 10/2012 | Grokop ............... A61B 5/1123 706/52 |
| 2013/0029681 A1* | 1/2013 | Grokop .................. G01C 21/16 455/456.1 |
| 2015/0173631 A1 | 6/2015 | Richards et al. |
| 2015/0272483 A1* | 10/2015 | Etemad .................... A61B 5/05 600/409 |
| 2015/0374240 A1 | 12/2015 | Lee |
| 2016/0058367 A1 | 3/2016 | Raghuram et al. |
| 2016/0089086 A1 | 3/2016 | Lin et al. |
| 2016/0120476 A1 | 5/2016 | Liu et al. |
| 2016/0166197 A1 | 6/2016 | Venkatraman et al. |

FOREIGN PATENT DOCUMENTS

| | | |
|---|---|---|
| WO | 2011032132 A2 | 3/2011 |
| WO | WO-2016069082 A1 | 5/2016 |

OTHER PUBLICATIONS

International Search Report and Written Opinion—PCT/US2017/057384—ISA/EPO—dated Jan. 26, 2018.

\* cited by examiner

CARDIOVASCULAR PARAMETER ESTIMATION IN THE PRESENCE OF MOTION

CROSS REFERENCE TO RELATED APPLICATIONS

This application claims the benefit of and priority to U.S. Provisional Patent Application No. 62/431,759 entitled "CARDIOVASCULAR PARAMETER ESTIMATION IN THE PRESENCE OF MOTION," filed Dec. 8, 2016, which is assigned to the assignee hereof and incorporated by reference herein in its entirety.

FIELD

This disclosure relates generally to apparatus, systems, and methods for performing biometric measurements including measurement of cardiovascular parameters such as heart rate.

BACKGROUND

Modern mobile devices may include sensors such as optical sensors, which are used to measure biometric information. For example, a photoplethysmogram (PPG) sensor obtains volumetric measurements of blood vessels near the skin surface. When the heart pumps blood, the resulting pressure pulse causes changes to blood vessels. The pressure pulse may distend arteries and arterioles in skin tissue. An optical sensor, such as a PPG sensor, may be used to detect a change in blood vessel volume caused by the pressure pulse. Blood vessel volume change caused by the pressure pulse may be detected by illuminating the skin with the light from a light-emitting diode (LED) and then measuring the amount of light either transmitted or reflected to a photodiode. Blood vessel volume change caused by blood flow to the skin may be modulated by various physiological parameters. Therefore, the information provided by PPG sensors may be used to obtain a variety of biometric measurements.

One drawback of blood volume sensors, such as PPG sensors, is that the biometric measurements obtained are sensitive to user movement. Thus, user movements can affect optical sensor measurements and introduce noise and other artifacts into the measured signals. Some techniques to address noise may use adaptive filters, which typically reduce noise based on motion related signals provided by an accelerometer. Adaptive filters use the motion related signals to compensate for motion induced noise in the optical sensor determined heart rate signal. However, for many activities, a higher activity rate may result in greater energy being expended and consequently a faster heart rate (e.g. more beats per minute). Thus, in many situations, heart rate may track the frequency of motion.

For activities with regular motion, the temporal frequencies related to the motion are present in the spectrum of both accelerometers and PPG sensors. The term "heart rate equal cadence" is used to refer to instances where a spectral component of the motion occurs at the same temporal frequency as a component of a cardiovascular parameter such as the heart rate. When heart rate equal cadence occurs, a separate heart rate signal may not be discernible, preventing heart rate estimation.

SUMMARY

According to some aspects, a processor-implemented method may comprise: obtaining a plurality of biometric sensor signal measurements of an biometric sensor signal, the biometric sensor signal measurements based, in part, on one or more cardiovascular parameters of a user; obtaining a plurality of motion sensor signal measurements of a motion sensor signal, the motion sensor signal measurements based, in part, on motion of the user; determining, based, in part, on the motion sensor signal measurements, an activity type; determining, based on the activity type, for each cardiovascular parameter in a subset of the one or more cardiovascular parameters, a corresponding likely cardiovascular parameter value; and determining, for each cardiovascular parameter in the subset, a corresponding fundamental frequency associated with the biometric sensor signal, based, in part, on the motion sensor signal measurements and the corresponding likely cardiovascular parameter value.

In another aspect, a device may comprise: a motion sensor, the motion sensor to output a motion sensor signal based, in part, on motion of a user; a biometric sensor, the biometric sensor to output a biometric sensor signal based, in part, on one or more cardiovascular parameters of the user; and a processor coupled to the motion sensor and the biometric sensor. In some embodiments, the processor may be configured to: obtain a plurality of biometric sensor signal measurements of the biometric sensor signal; obtain a plurality of motion sensor signal measurements of the motion sensor signal; determine, based, in part, on the motion sensor signal measurements, an activity type; determine, based on the activity type, for each cardiovascular parameter in a subset of the one or more cardiovascular parameters, a corresponding likely cardiovascular parameter value; and determine, for each cardiovascular parameter in the subset, a corresponding fundamental frequency associated with the biometric sensor signal, based, in part, on the motion sensor signal measurements and the corresponding likely cardiovascular parameter value.

In a further aspect, a device may comprise: means for obtaining a plurality of biometric sensor signal measurements of an biometric sensor signal, the biometric sensor signal measurements based, in part, on one or more cardiovascular parameters of a user; means for obtaining a plurality of motion sensor signal measurements of a motion sensor signal, the motion sensor signal measurements based, in part, on motion of the user; means for determining, based, in part, on the motion sensor signal measurements, an activity type; means for determining, based on the activity type, for each cardiovascular parameter in a subset of the one or more cardiovascular parameters, a corresponding likely cardiovascular parameter value; and means for determining, for each cardiovascular parameter in the subset, a corresponding fundamental frequency associated with the biometric sensor signal, based, in part, on the motion sensor signal measurements and the corresponding likely cardiovascular parameter value.

In some embodiments, a non-transitory computer-readable medium may comprise executable instructions to configure a processor to: obtain a plurality of biometric sensor signal measurements of an biometric sensor signal, the biometric sensor signal measurements based, in part, on one or more cardiovascular parameters of a user; obtain a plurality of motion sensor signal measurements of a motion sensor signal, the motion sensor signal measurements based, in part, on motion of the user; determine, based, in part, on the motion sensor signal measurements, an activity type; determine, based on the activity type, for each cardiovascular parameter in a subset of the one or more cardiovascular parameters, a corresponding likely cardiovascular parameter value; and determine, for each cardiovascular parameter in the subset, a corresponding fundamental frequency associated with the biometric sensor signal, based, in part, on the motion sensor signal measurements and the corresponding likely cardiovascular parameter value.

Embodiments disclosed also relate to hardware, software, firmware, and program instructions created, stored, accessed, or modified by processors using computer readable media or computer-readable memory. The methods described may be performed on processors and various user equipment.

These and other embodiments are further explained below with respect to the following figures. It is understood that other aspects will become readily apparent to those skilled in the art from the following detailed description, wherein it is shown and described various aspects by way of illustration. The drawings and detailed description are to be regarded as illustrative in nature and not as restrictive.

BRIEF DESCRIPTION OF THE DRAWINGS

Embodiments of the invention will be described, by way of example only, with reference to the drawings.

Figure 1:
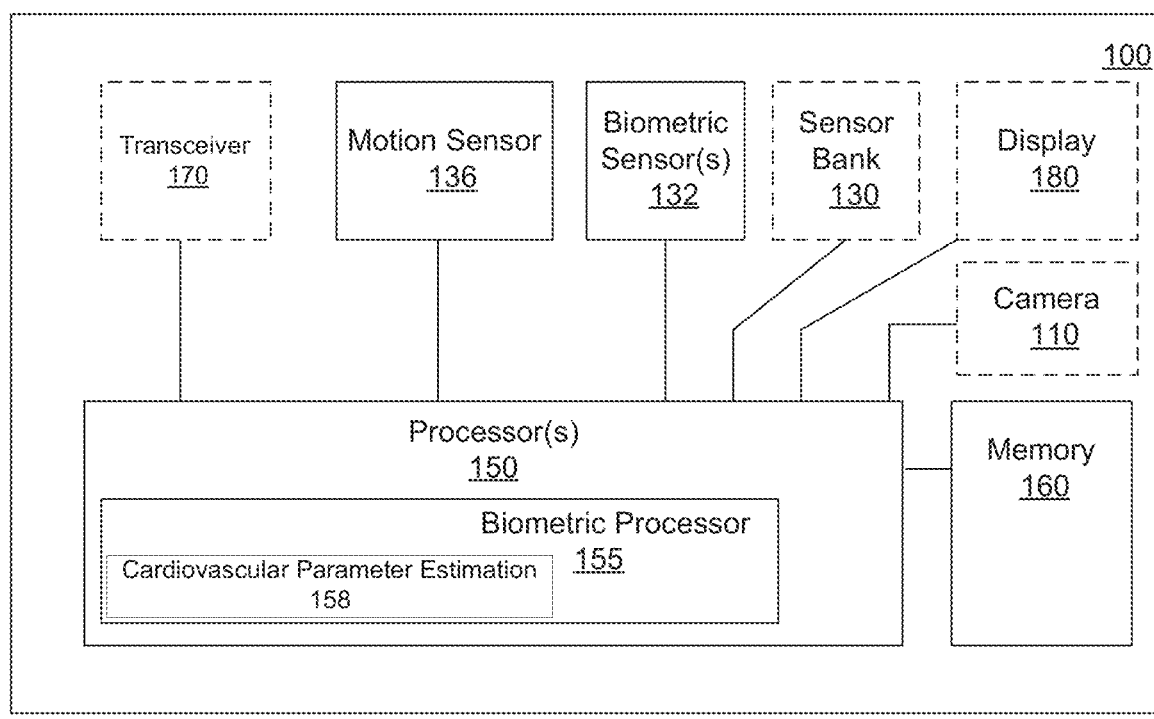
FIG. 1 shows a block diagram of exemplary device capable of obtaining biometric information in a manner consistent with disclosed embodiments.

Like numbered entities in different figures may correspond to one another. Reference to a numbered entity in any figure may therefore correspond to any like numbered entity in any other figure.

DETAILED DESCRIPTION

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for the purpose of providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the disclosure.

In the figures described below, one or more of the blocks shown may perform various functions. The blocks shown in the figures are merely exemplary and the functions associated with the blocks may be split or combined in various ways in a manner consistent with disclosed embodiments. For example, the logical entities shown may be implemented using physically separate components/devices, or, one or more of the logical entities may be included in a single physical component/device.

Biometric information (e.g. cardiovascular information) may be obtained using biometric sensors on mobile devices including wearable devices. For example, biometric information is often obtained based on measurements by optical sensors (e.g. PPG sensors). For example, user cardiovascular measurements may be used to obtain heart rate, which is used in a variety of biometric calculations. The term "cardiovascular parameter" is used to refer to one or more of heart rate, oxygen saturation, blood pressure, pulse wave velocity, etc., or parameters that may be derived from one or more of the above parameters. The terms "cardiovascular measurements" or "cardiovascular parameter measurements" refer to measurements of any of the above parameters.

Depending on the application, heart rate and/or other cardiovascular parameters may be determined: 1) continuously over some period; 2) periodically, in the background; and/or 3) in one-shot mode on user demand. However, conventional cardiovascular measurements and/or heart rate determination techniques are often affected detrimentally by user movement. For example, noise, which may be caused by user movement, can degrade the quality of signals used to make cardiovascular measurements thereby producing inaccuracies, or in some instance, making the determination of heart rate or other cardiovascular parameters challenging.

To compensate for user motion, motion related measurements provided by an accelerometer may be input to an adaptive filter to facilitate noise reduction. Conventionally, some adaptive filters may use the motion related signals to compensate for and/or remove motion induced noise in the cardiovascular and/or heart rate signal in the time domain. However, when motion related frequencies (e.g. in measurements by the motion sensor) closely track frequencies related to the heart rate or one or more cardiovascular parameters (e.g. in measurements by the biometric sensor), determination of a heart rate and/or other cardiovascular parameters can be challenging.

Some disclosed embodiments improve the accuracy and/or reliability of measured signals relating to one or more cardiovascular parameters (e.g. heart rate) from a biometric sensor (e.g. optical sensors, PPG sensors, ultrasonic sensors etc). In some embodiments, robust estimation of one or more cardiovascular parameters using biometric sensors coupled to a motion sensor (e.g. accelerometers, inertial measurement units (IMUs), gyroscopes etc) may be facilitated, in part, by using a physiological model to determine likely values of the one or more cardiovascular parameters. In some embodiments, a final or refined value of the one or more cardiovascular parameters may then be estimated based on the biometric sensor measurements and the likely values of the one or more cardiovascular parameters (e.g. heart rate).

The term "physiological model" as used herein may include one or more of: (a) a history of physiological or cardiovascular measurements (e.g. heart rate) including an average or typical value associated with the measurements (e.g. a rest heart rate), which may further be classified by day of week, time of day, period, and/or time intervals; (b) a history of physiological or cardiovascular measurements (e.g. heart rate) classified by activity type (e.g. walking, running, hiking, climbing, rowing, swimming, dancing, biking, yoga etc.). Further, the history of physiological measurements associated with each activity type may include: (i) physiological measurements at various time points during the activity relative to the start of the corresponding activity and/or (b) a prior range, or prior maximum and/or prior minimum recorded values for the cardiovascular measurements (e.g. a heart rate range, or a maximum or minimum heart rate) associated with the corresponding activity type and/or (c) statistical parameters such as an average, median, standard deviation, and/or variance, for the cardiovascular parameter and activity type. In some embodiments, the activity type may also be associated with a time period during which the activity occurs (e.g. day of week, time of day etc). In some embodiments, the time period may be determined based on a user calendar entry (e.g. on device 100) indicating that the activity is performed during some time period. In some embodiments, the physiological model may be: (i) specific to a user based on a history of recorded measurements for that user, and/or (ii) default measurements based on expected or typical measurements over a larger population sample. In some embodiments, the activity type may be determined based on user input or user selection and/or received from an application running on device 100 and/or an activity tracker device (or application) coupled to device 100.

As one example, the physiological model may associate an activity type (e.g. running) with a day of the week (e.g. Tuesday) and/or a time period (e.g. between 5-7 pm). Further, the model may include aggregated sensor measurements associated with the activity type (e.g. running). In some embodiments, the aggregated measurements may include statistical measures such as a measure of central tendency (e.g. an average, median, and/or mode) standard deviation, variance and/or other metrics. In the example above, the physiological model may initially infer an activity type based on the day of week and time period (e.g. running—if it is Tuesday at 6 pm). The activity type may then be verified against the prior history of aggregated measurements. If motion sensor measurements fall within a range for the activity (e.g. running), the physiological model may output the activity type and one or more estimates for cardiovascular parameters (e.g. heart rate) such as one or more of: a range, a maximum, a minimum, an average, a standard deviation, a variance, etc. associated with the activity type.

In some embodiments, one or more measurements used to obtain the physiological model may be obtained from application(s) on a device (e.g. a wearable device) or a coupled device (such as a smartphone coupled to a smartwatch) that tracks the activity. As one example, when an application related to rowing is started, the initiation of the application or parameters provided by the application (e.g. through an API and/or over a communication interface—which may be wireless) may be used to determine/infer the activity type and/or obtain a history of prior measurements. For example, a wearable activity tracker may provide the activity type, start time, measurements and/or other information via a Wireless Personal Area Network (WPAN) to a device determining cardiovascular measurements.

In some embodiments, an activity type may be inferred from motion sensor measurements. For example, repetitive patterns in accelerometer measurements (steps, impact, motion sequences, etc) may be used to identify a motion signature or unique pattern (present in and/or determined from) motion sensor signals associated with the corresponding activity. The signature or pattern may be used to infer the type of activity. For example, a stored database of measurements, measurement patterns or measurement signatures associated with activities may be used to determine a likely activity type.

In some embodiments, the motion sensor measurements may be used to determine spectral power in the motion sensor signal. The spectral power may be correlated with an activity type. For example, based on the value of the integrated power in the motion sensor signal, an activity type may be inferred. The activity type may be used, for example, by a physiological model to determine likely values of a cardiovascular parameter (e.g. a likely heart rate), a range (e.g. a likely heart rate range) and other statistical measures related to the cardiovascular parameters being determined.

In some embodiments, based, in part, on the activity type and/or a physiological model, a likely value of one or more cardiovascular parameters (e.g. heart rate) may be estimated. Thus, parameters in the motion sensor spectral pattern and/or parameters derived from the motion sensor spectral pattern may be used to determine: (i) an activity type (e.g. running, bicycling etc.); (ii) an likely value for a cardiovascular parameter based on the activity type; and/or (iii) statistical measures related to the cardiovascular parameter based on the activity type. In some embodiments, the likely value of the one or more cardiovascular parameters (e.g. likely heart rate) may be used to determine an estimated value of the one or more cardiovascular parameters (e.g. a raw heart rate).

In some embodiments, determination of the estimated value of the one or more cardiovascular parameters may be based further on spectral frequency components present in a motion sensor and/or biometric sensor spectrogram. In some embodiments, the likely value of the one or more cardiovascular parameters (e.g. likely heart rate) may be used or reported as the estimated or measured value of the one or more cardiovascular parameters (e.g. raw heart rate) in situations where spectral frequency components of the one or more cardiovascular parameters (e.g. heart rate) are not easily distinguishable from spectral components of motion.

These and other techniques are further explained below with respect to the figures. It is understood that other aspects will become readily apparent to those skilled in the art from the following detailed description, wherein it is shown and described various aspects by way of illustration. The drawings and detailed description are to be regarded as illustrative in nature and not as restrictive.

FIG. 1 shows a block diagram of exemplary device 100 capable of obtaining biometric information in a manner consistent with disclosed embodiments.

In FIG. 1, device 100, may take the form of a mobile station or mobile device such as a wearable device. Device 100 may be (or may include sections or components) proximate to and/or in contact with the user's skin tissue. In some embodiments, device 100 may be in contact with an optically and/or an ultrasonically transparent surface, where the surface is proximate to, or in contact with the user's skin tissue.

In general, the term "skin" or "skin tissue," as used herein, is used to refer to cutaneous tissue, or an optically (or ultrasonically) transparent surface in contact with or in close proximity to cutaneous tissue. In addition, the term "movement relative to skin" or "movement of the sensor relative to the skin" is used to refer to movement of any body part under the biometric sensor(s) (e.g. on device 100) relative to the biometric sensor(s) 132 measuring one or more cardiovascular parameters. The body parts include skin, bones, cutaneous tissue, subcutaneous tissue, etc, under the biometric sensor(s) all of which may affect measurements by the biometric sensor(s) 132 when there is relative motion. The term "cardiovascular" is used to refer to the circulatory system including the heart, blood, and blood vessels. The term "cardiovascular parameter" is used to refer to any parameter that is measured by device 100 and/or biometric sensor(s) 132 (e.g. directly), or that may derived (e.g. indirectly) from measurements by device 100 and/or biometric sensor(s) 132. Measurements of the one or more parameters associated with a user's cardiovascular system may be used to obtain various biometric information, including a user's heart rate, oxygen saturation, blood pressure, pulse wave velocity, etc.

In general, device 100 may take the form of any mobile or wearable device such as a watch, wristband, ear plug, chest band, head band, arm, shoulder, leg or ankle cuff, and/or another device in contact with skin. In some embodiments, the wearable portion (e.g. watch, wristband, ear plug, chest band, head band, arm, shoulder, leg or ankle cuff etc.), which may include biometric sensor(s) 132, may form part of device 100. In general, the devices and techniques disclosed herein may be used in conjunction with biometric measurements, in instances where motion induced noise may detrimentally affect the accuracy and/or reliability of the biometric measurements.

The terms "biometric sensor" and "motion sensor" are used herein to refer to one or more of the respective types of sensors. Further, the term "biometric sensor" is used to refer to any type of sensor such as optical sensors, PPG sensors, ultrasonic sensors, etc., which may be used to measure cardiovascular parameters (e.g. heart rate) and where the signals and/or measurements by the biometric sensor may be affected by motion artifacts (e.g. caused by motion of the subject). The term "accuracy" refers to the proximity of a measurement of a parameter to an ideal or actual value of the parameter. The term "reliability" refers to the degree of variation in accuracy over a series of measurements.

In some embodiments, device 100 may provide functionality associated with a cellular phone, mobile phone, other wireless communication device and/or a wearable device coupled to a wireless communication device. For example, device 100 may be capable of (or operationally coupled to a device capable of) receiving wireless communication and/or navigation signals. For example, device 100 (e.g. a mobile phone) may include components or portions that are in contact with a user's skin and operationally coupled to device 100 (e.g. the mobile phone). As another example, device 100 may take the form of a wearable computing device, which may also include biometric sensor(s) 132, a display 180 and/or a camera 110 paired to a wearable headset, which may include various other components. For example, the headset may include a head mounted display (HMD), which may be used to display live and/or real world images.

In some embodiments, device 100 may be a standalone biometric measurement device. The biometric measurement device may, in some instances, be incorporated into another device such as an activity tracker, gaming or other device that may not be configured to connect to a network or to otherwise communicate, either wirelessly or over a wired connection, with another device. For example, device 100 may omit communication elements and/or networking functionality. Thus, in some embodiments, all or part of one or more of the techniques described herein may be implemented in a standalone device that may not be configured to connect using wired or wireless networking with another device.

As shown in FIG. 1, an example device 100 may include motion sensor 136, biometric sensors 132 (e.g. optical sensors, PPG sensors, ultrasonic sensors etc.), one or more processor(s) 150 (hereinafter referred to as "processor(s) 150"), and memory 160. Device 100 may optionally include one or more of: sensor bank 130, camera(s) 110, display 180, and/or transceiver 170. The various components listed above may be operatively coupled to each other and to other functional units (not shown) on device 100 through connections such as buses, lines, fibers, links, etc., or some combination thereof.

When included, camera(s) 110 may comprise charge coupled devices (CCD), complementary metal oxide semiconductor (CMOS), and/or various other image sensors. Camera(s) 110, which may be still or video cameras, may capture a series of image frames of an environment and send the captured image frames to processor(s) 150. In some embodiments, images from camera 110 may be used, in part, to determine user motion. When included, display 180 may comprise one or more of: a screen, touchscreen, HMD, etc capable of displaying Graphical User Interfaces (GUIs), accepting user input, displaying results, rendering images, including color images etc. In some embodiments, camera(s) 110, display 180, and/or one or more other components of device 100 may be may be operatively coupled to, but housed separately from device 100.

In some embodiments, device 100 may optionally include transceiver 170. Transceiver 170 may, for example, include a transmitter enabled to transmit one or more signals over one or more types of wireless communication networks and a receiver to receive one or more signals transmitted over the one or more types of wireless communication networks. Transceiver 170 may facilitate communication with wireless networks based on a variety of technologies such as, Wireless Personal Area Networks (WPANs) such Bluetooth, Near Field Communication (NFC), networks based on the IEEE 802.15x family of standards, etc. In some embodiments, transceiver 170 may also facilitate communication with femtocells, Wi-Fi networks or Wireless Local Area Networks (WLANs), which may be based on the IEEE 802.11 family of standards, and/or Wireless Wide Area Networks (WWANs) such as LTE, WiMAX, etc. For example, in some embodiments, transceiver 170 may facilitate communication with another device such as a server, cell phone, and/or other computing device, which may be coupled to one or more of the various networks described above.

For example, the transceiver 170 may facilitate communication (directly or indirectly) with a WWAN such as a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, Long Term Evolution (LTE), WiMax, and so on. A CDMA network may implement one or more radio access technologies (RATs) such as cdma2000, Wideband-CDMA (W-CDMA), and so on. Cdma2000 includes IS-95, IS-2000, and IS-856 standards. A TDMA network may implement Global System for Mobile Communications (GSM), Digital Advanced Mobile Phone System (D-AMPS), or some other RAT. GSM, W-CDMA, and LTE are described in documents from an organization known as the "3rd Generation Partnership Project" (3GPP). Cdma2000 is described in documents from a consortium named "3rd Generation Partnership Project 2" (3GPP2). 3GPP and 3GPP2 documents are publicly available. The techniques disclosed herein may be implemented in conjunction with any combination of WWAN, WLAN and/or WPAN.

For example, one or more measurements obtained by motion sensor 136 and/or biometric sensor 132 on a device 100 may be sent using transceiver 170 to another device (e.g. a mobile phone) that may be communicatively coupled to device 100. The mobile phone may process the measurements in accordance with disclosed techniques and send results back to device 100, which may be receive the results through transceiver 170. The received results may be further processed by processor (s) 150 and/or displayed using optional display 180.

As another example, a device (e.g. a mobile device) may comprise a wearable portion (e.g. a smartwatch) with biometric sensor 132 and/or motion sensor 136, which may send measurements over a WPAN (e.g. Bluetooth) connection to processor(s) 150, which may process the measurements and cause results to be displayed on display 180. Display 180 may form part of one or more of: the wearable portion (e.g. the smartwatch) of device 100, device 100 (e.g. the non-wearable portion of the mobile device), and/or housed separately (e.g. as a head mounted display).

In some embodiments, camera 110, transceiver 170, and/or one or more other components on device 100 may be omitted. Embodiments disclosed herein may be used in a standalone device, for example, in a wearable device that does not include a camera, transceiver 170 and/or communicate with another device. Thus, in some embodiments, device 100 may obtain measurements from motion sensor 136 and/or biometric sensor 132. The measurements may be processed by processor(s) 150 using biometric processor 155 and/or cardiovascular parameter estimation (CPE) processor 158 and/or processed based on routines stored in memory 160. The results obtained (e.g. an estimated heart rate) may be optionally displayed on display 180.

In some embodiments, biometric sensor 132 may be an optical sensor, a PPG sensor, ultrasonic sensor etc. For example, a biometric sensor may take the form of one or more PPG sensors and/or other sensors that use optical techniques such as photoplethysmography or impedance plethysmography to obtain biometric measurements, including blood volume measurements. For example, an optical sensor may output electrical signals based on photometric measurements related to volumetric changes in blood vessels in skin tissue and/or other measurements of cardiovascular parameters. Various optical sensors are known and available (e.g. Analog Devices ADPD142RG/ADPD142RI). For example, optical sensors may be designed to stimulate LEDs and measure the corresponding optical return signals.

The optical return signals may be sent to processor(s) 150 and/or, in some instances, may be used to estimate some biometric information such as one or more cardiovascular parameters (e.g. heart rate). Optical sensor may include photodiodes and/or LEDs to output light and measure corresponding optical return signals. Biometric sensor 132 may also take the form of an ultrasonic sensor where a reflected ultrasonic signal (such as an ultrasonic pulse) may be used to detect the motion of a blood vessel wall and obtain cardiovascular parameter (e.g. heart rate) information.

In some embodiments, biometric sensor 132 may measure one or more parameters associated with a user cardiovascular system and provide biometric and/or cardiovascular parameter related (e.g. heart rate) information. In some embodiments, the biometric (e.g. cardiovascular parameter measurements such as heart rate) related information may be provided at some specified rate. For example, biometric sensor 132 may provide measured samples at a user-specified or default sampling rate to processor(s) 150. In some embodiments, the sampling rate of biometric sensor 132 may be configurable. For example, for heart rate related measurements, biometric sensor 132 typically provides samples at a rate greater than twice a maximum heart rate. For example, a sampling rate of 20 Hz may be used. In some embodiments, the samples provided by biometric sensor 132 may be buffered in memory 160 and conditioned prior to being processed by processor(s) 150.

In certain example implementations, device 100 may also include motion sensor 136, which may take the form of an Inertial Measurement Unit (IMU) and/or accelerometers and/or gyroscopes. Motion sensor 136 may include one or more gyroscopes and/or one or more accelerometers. Motion sensor 136 may be a Micro Electro-Mechanical System (MEMS) based sensors. Motion sensor 136 may provide movement related information to processor(s) 150. In some embodiments, the movement related information may be provided at some specified rate. For example, motion sensor 136 may provide measured samples at a user-specified or default sampling rate to processor(s) 150. In some embodiments, the sampling rate of motion sensor 136 may be configurable. In some embodiments, the samples provided by motion sensor 136 in some predetermined or configured time window may be conditioned and buffered in memory 160 and prior to being processed by processor(s) 150. Device 100 may also optionally include sensor bank 130, which may include various other sensors such as ambient light sensors, acoustic sensors, electromechanical sensors, etc.

Further, in some embodiments, the time window over which the sample measurements are obtained (e.g. from biometric sensor 132) may be configurable. In some embodiments, the time window may be user configurable or default to one of several options based on an operating mode of device 100. For example, the time window may be adjusted based on input from a physiological model related to a user activity type. In some embodiments, the activity type may be inferred from motion sensor measurements (e.g. from motion sensor 136) and, based on the inferred activity type, a physiological model may provide input to processor(s) 150 to configure a time window for measurements. In some embodiments, the time window may be configured based further on whether the measurements are being captured continuously, or in a "one shot" mode, and/or based on the available memory and desired response time, and/or accuracy/reliability constraints set by the user.

In some embodiments, a heart rate range, a maximum heart rate, and/or minimum heart rate, and/or a sampling interval may be set, reset, and/or provided to processor(s) 150 based on one or more of: motion sensor signal measurements (e.g. from motion sensor 136), activity type, and/or input from a physiological model. For example, based on motion sensor measurements, an activity type may be determined. Further, based on a physiological model associated with the activity type, device 100 may dynamically determine a user's likely heart rate, and/or determine that the user's heart rate range is between a maximum heart rate and a minimum heart rate.

Processor(s) 150 may execute software to process measurements by biometric sensor 132, motion sensor 136, and/or sensor bank 130. Processor(s) 150 may be implemented using some combination of hardware, firmware, and software. Processor(s) 150 may represent one or more circuits configurable to perform at least a portion of a computing procedure or process related to processing sensor measurements and/or obtaining biometric information (e.g. cardiovascular parameters such as heart rate) derived from the measurements. Processor(s) 150 may retrieve instructions and/or data from memory 160. In some embodiments, processor(s) 150 may comprise biometric processor 155, which may execute or facilitate the execution of various biometric applications. In some embodiments, processor(s) 150 may also comprise exemplary cardiovascular parameter estimation (CPE) processor 158, which may facilitate cardiovascular parameter estimation as outlined further in the disclosure.

In some embodiments, processor(s) 150 may include biometric processor 155 and/or CPE processor 158, which may be implemented using some combination of hardware and software. For example, in one embodiment, biometric processor 155 and/or CPE processor 158 may be implemented using software and/or firmware. In another embodiment, dedicated circuitry, such as Application Specific Integrated Circuits (ASICs), Digital Signal Processors (DSPs), etc. may be used to implement biometric processor 155 and/or CPE processor 158. In some embodiments, biometric processor 155 and/or CPE processor 158 may include functionality to communicate with one or more other processors and/or other components on device 100.

In some embodiments, input from biometric sensor 132 and motion sensor 136, and/or biometric information derived (e.g. by biometric processor 155) from cardiovascular measurements by biometric sensor 132 and/or motion sensor 136 may be provided to CPE processor 158, which may output cardiovascular parameters such as a heart rate and/or one or more quality metrics associated with the output cardiovascular parameters (e.g. heart rate). In some embodiments, the measured signals from biometric sensor 132 and motion sensor 136 may be buffered in memory 160 and conditioned prior to being processed by processor(s) 150, biometric processor 155, and/or CPE processor 158. For example, the buffered signals may processed by clamping to remove noise spikes, passing the signals through a high pass filter to remove DC and low frequency components and analyzed statistically to discard outliers.

All or part of memory 160 may be co-located (e.g., on the same die) with processors 150 and/or located external to processors 150. Processor(s) 150 may be implemented using one or more application specific integrated circuits (ASICs), central and/or graphical processing units (CPUs and/or GPUs), digital signal processors (DSPs), digital signal processing devices (DSPDs), programmable logic devices (PLDs), field programmable gate arrays (FPGAs), controllers, micro-controllers, microprocessors, embedded processor cores, electronic devices, other electronic units designed to perform the functions described herein, or a combination thereof, to name a few examples.

Memory 160 may represent any type of long term, short term, volatile, nonvolatile, or other memory and is not to be limited to any particular type of memory or number of memories, or type of physical media upon which memory is stored. In some embodiments, memory 160 may hold code (e.g. instructions that may be executed by one or more processors) to facilitate various biometric and/or cardiovascular (e.g. heart rate) estimation methods. Memory 160 may also include buffers to store the signal measurements received from motion sensor 136 and biometric sensor 132 and to store intermediate data and processed results.

In some embodiments, memory may hold code and data for physiological models, which may be used to provide input to processor(s) 150. The physiological model may be an application running on processor(s) 150. In some embodiments, the data for the physiological models may include stored measurements from sensors and/or other aggregated sensor measurement information, and/or statistical information derived from sensor measurements. Information associated with or determined by the physiological model may be stored in one or more databases in memory 160.

In general, memory 160 may represent any data storage mechanism. Memory 160 may include, for example, a primary memory and/or a secondary memory. Primary memory may include, for example, a random access memory, read only memory, etc. While illustrated in FIG. 1 as being separate from processors 150, it should be understood that all or part of a primary memory may be provided within or otherwise co-located and/or coupled to processors 150. For example, in one embodiment, conditioned signal measurements from biometric sensor 132 and/or motion sensor 136 may be stored in primary memory.

Secondary memory may include, for example, the same or similar type of memory as primary memory and/or one or more data storage devices or systems, such as, for example, flash/USB memory drives, memory card drives, disk drives, optical disc drives, tape drives, solid state drives, hybrid drives etc. In certain implementations, secondary memory may be operatively receptive of, or otherwise configurable to couple to a computer-readable medium in a removable media drive (not shown) coupled to device 100. In some embodiments, a non-transitory computer readable medium may form part of memory 160 and/or processor(s) 150.

Not all components comprised in device 100 have been shown in FIG. 1. Further, device 100 may also be modified in various ways in a manner consistent with the disclosure, such as, by adding, combining, or omitting one or more of the functional blocks shown. For example, in some configurations, device 100 may not include transceiver 170. In some embodiments, portions of device 100 may take the form of one or more chipsets, and/or the like.

Figure 2:
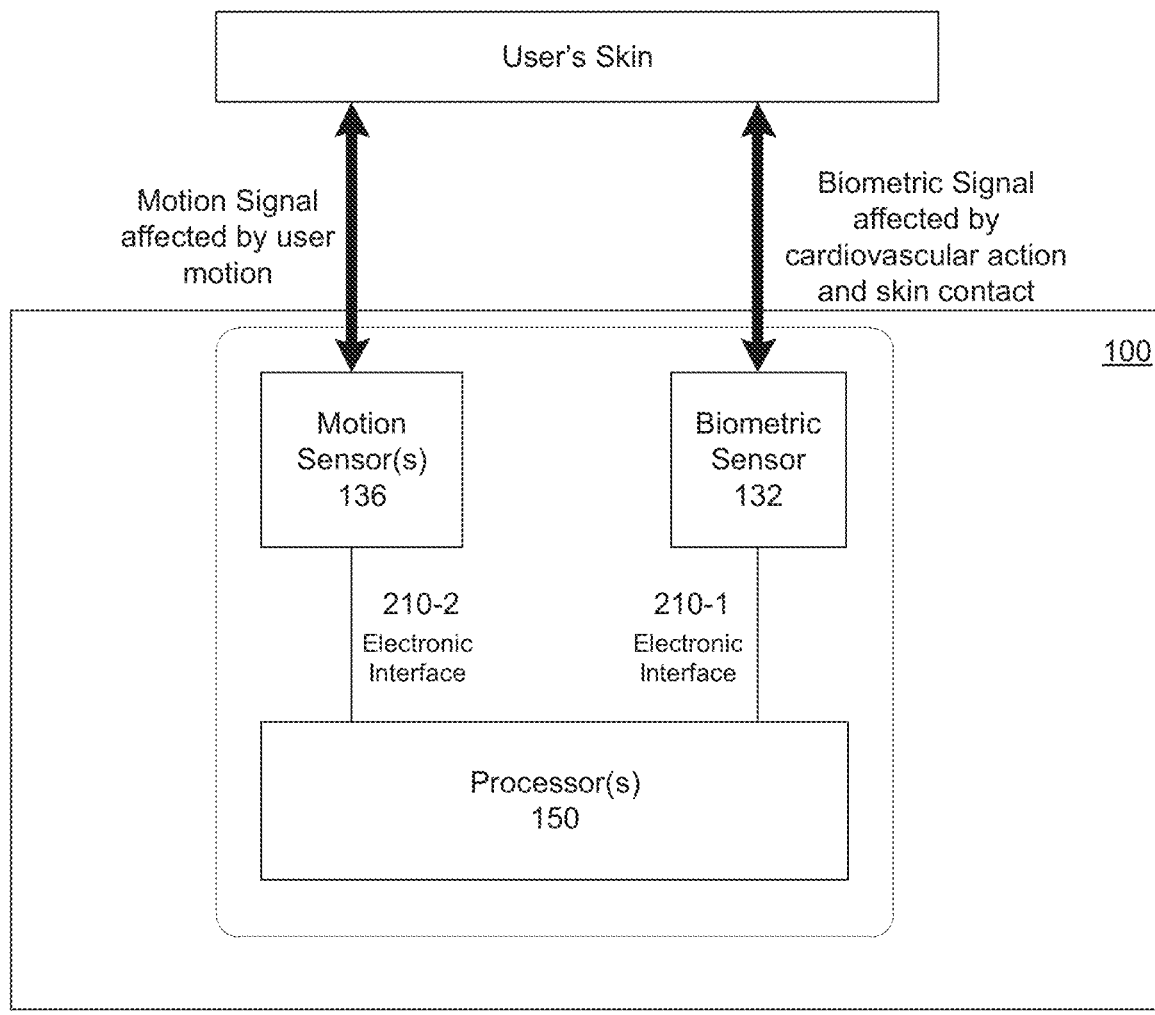
FIG. 2 shows a device with a biometric sensor, which may measure and output biometric signal samples related to biometric/cardiovascular parameters (e.g. volumetric measurements of blood vessels and/or heart rate).

FIG. 2 shows device 100 with biometric sensor 132, which may measure and output biometric signal samples related to cardiovascular parameters (e.g. volumetric measurements of blood vessels near the skin surface). The biometric signal measurement samples (e.g. from biometric sensor 132) may be input to one or more of processor(s) 150, biometric processor 155 and/or CPE processor 158. Because of user movements, biometric sensor signal measurement samples may contain noise or other artifacts. For example, if the amount of skin contact varies the quality of the biometric sensor signal measurements may be affected.

In some embodiments, motion sensor 136 may measure motion relative to skin and output signal samples dependent on the motion. In some embodiments, signals from both biometric sensor 132 and motion sensor 136 may be output via electronic interfaces 210-1 and 210-2, respectively, to processor(s) 150. In some embodiments, electronic interfaces 210-1 and 210-2 may perform a portion of the conditioning of signals from biometric sensor 132 and motion sensor 136. The conditioned signals may be buffered (e.g. in memory 160) and processed by processor(s) 150.

Figure 3A:
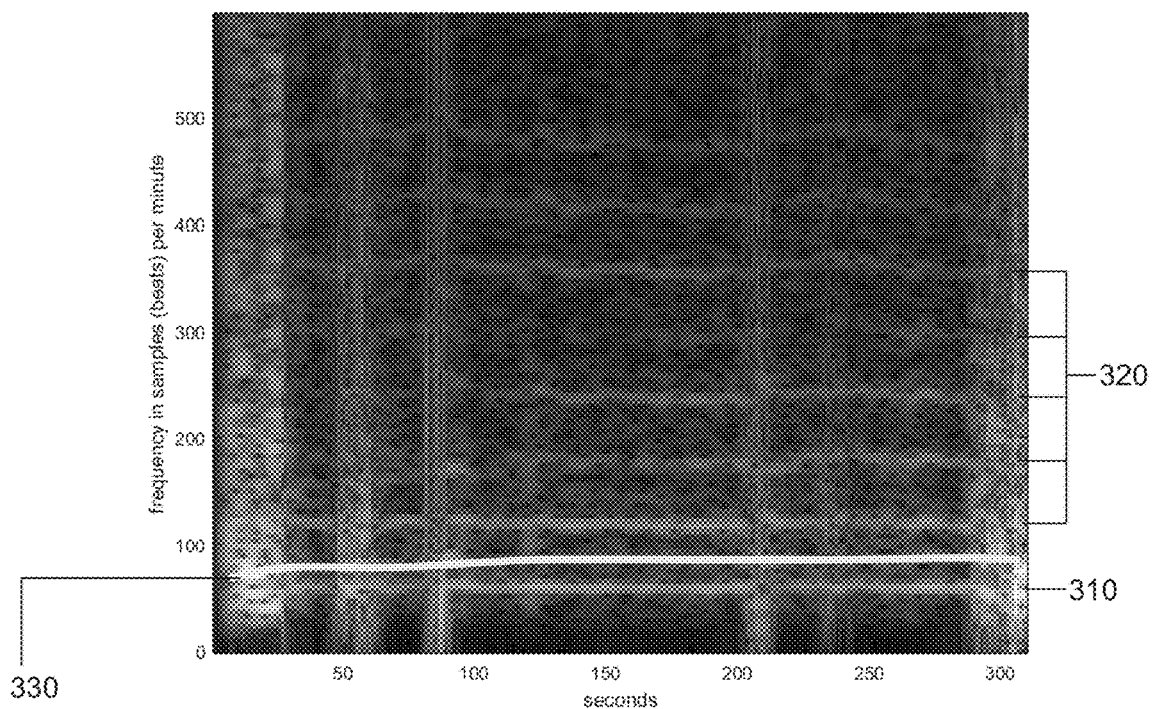
FIG. 3A shows an example spectrogram based on the output of a PPG sensor depicting frequencies (in beats per minute) present over some time period.
Figure 3B:
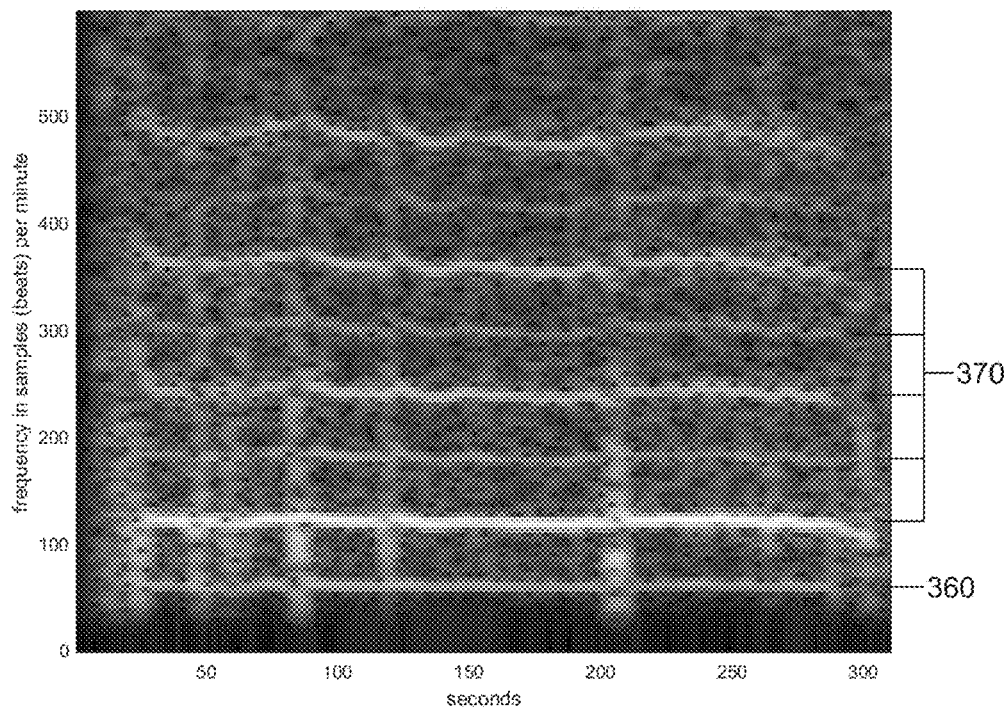
FIG. 3B shows another example spectrogram based on the output of a motion sensor depicting frequencies (in beats per minute) present over some time period.

FIG. 3A shows an example spectrogram 300 based on the output of a PPG sensor depicting frequencies (in beats per minute) present over some time period. FIG. 3B shows an example spectrogram 350 based on the output of a motion sensor depicting frequencies (in beats per minute) present over some time period. In FIGS. 3A and 3B, the power spectra data is plotted with the vertical axis in beats per minute and the intensity of the plot represents the power at that frequency and time.

The frequencies shown in the spectrograms of FIGS. 3A and 3B may be obtained, for example, from the corresponding (PPG or motion sensor) buffered time domain signal using Fast Fourier Transform (FFT) or similar techniques. The magnitudes of the FFT of the input biometric and motion signals may be squared to obtain the corresponding power spectrum for each signal.

The frequencies shown in FIGS. 3A and 3B may include a fundamental frequency related to a periodic physical event and multiples or "harmonics" of the fundamental frequency. The term "fundamental frequency" is used to refer to the lowest frequency produced by a measured periodic, oscillatory, or harmonic event. For example, a fundamental frequency associated with biometric sensor 132 may be related to the heart rate of a user. A fundamental frequency associated with motion sensor 136 may be related to a user motion or an activity type (e.g. running etc).

Spectrogram 300 in FIG. 3A shows a motion related frequency 310 (at approximately 60 beats per minute) and harmonics 320 of the motion related frequency. Spectrogram 350 in FIG. 3B also shows a corresponding motion related frequency 360 (at approximately 60 beats per minute) and harmonics 370 of the motion related frequency. From a comparison of frequencies present in spectrograms 300 and 350, frequency 330 (approximately 75 beats per minute), which is present in the PPG spectrogram 300 but not in the motion sensor spectrogram 350 may be determined to be the heart rate. Frequency 330, which is present in PPG spectrogram but not in motion sensor spectrogram 350, may be selected as an estimated heart rate.

Figure 4A:
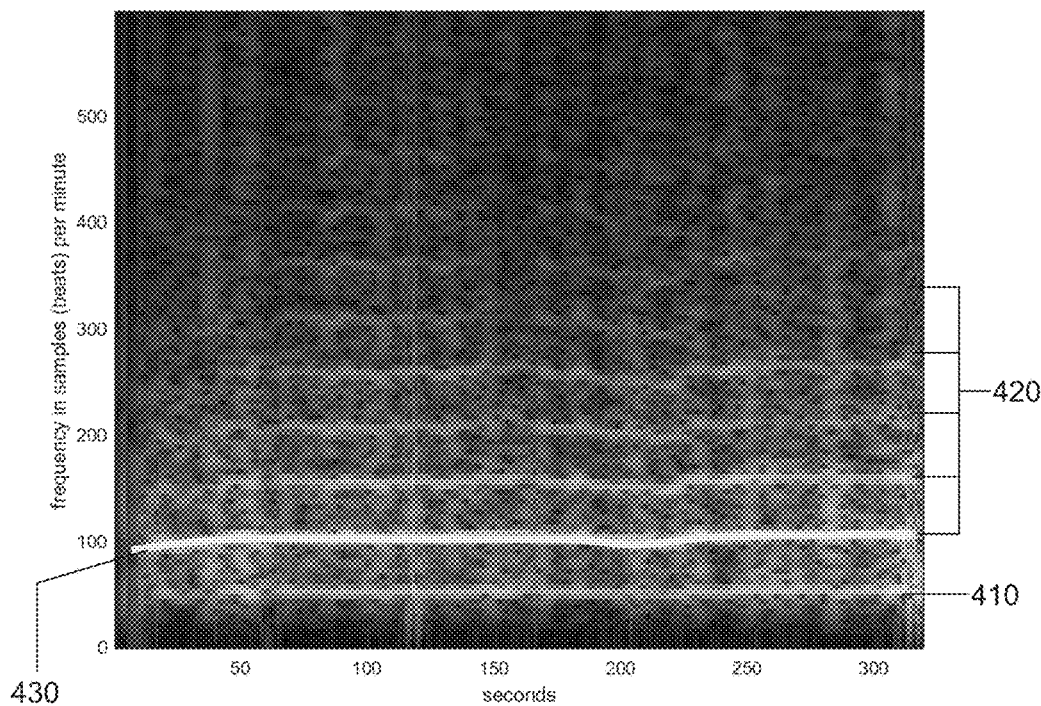
FIG. 4A shows an example spectrogram based on the output of a PPG sensor depicting frequencies (in beats per minute) present over some time period.
Figure 4B:
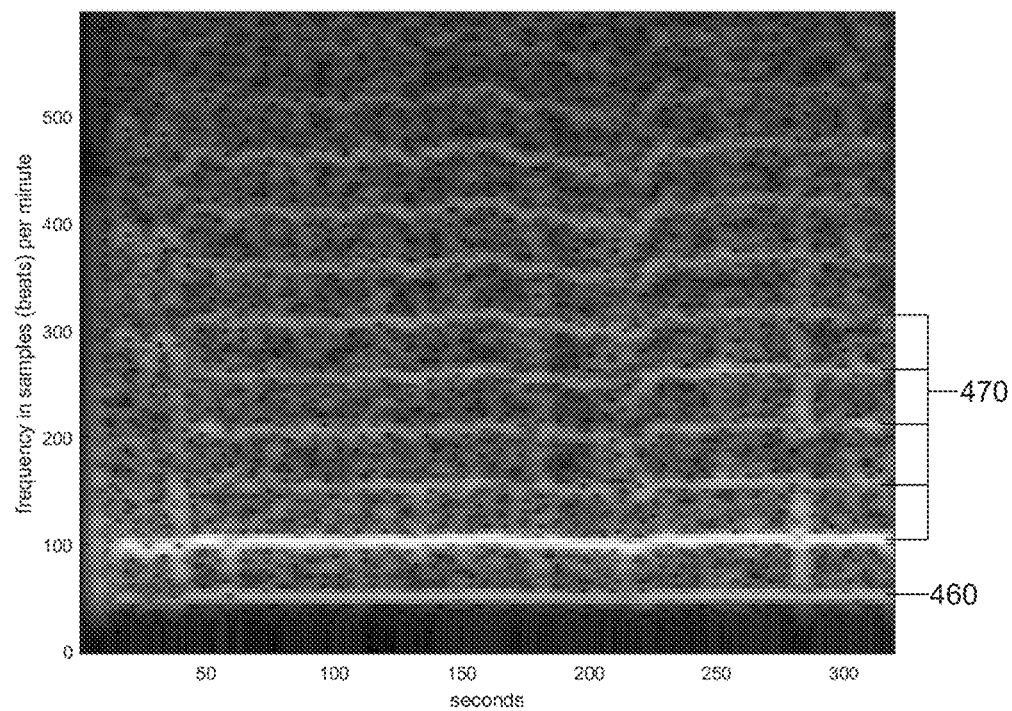
FIG. 4B shows a further example spectrogram based on the output of a motion sensor depicting frequencies (in beats per minute) present over some time period.

FIG. 4A shows an example spectrogram 400 based on the output of a PPG sensor depicting frequencies (in beats per minute) present over some time period. FIG. 4B shows an example spectrogram 450 based on the output of a motion sensor depicting frequencies (in beats per minute) present over some time period.

The frequencies shown in the spectrograms of FIGS. 4A and 4B may be obtained, for example, from the corresponding (PPG or motion sensor) buffered time domain signal using Fast Fourier Transform (FFT) or similar techniques. The magnitudes of the FFT of the input biometric and motion signals may be squared to obtain the corresponding power spectrum for each signal. Further, in FIGS. 4A and 4B, the power spectra data is plotted with the vertical axis in beats per minute and the intensity of the plot representing the power at that frequency and time.

Spectrogram 400 in FIG. 4A shows a motion related frequency 410 (at approximately 50 beats per minute) and harmonics 420 of the motion related frequency. Spectrogram 450 in FIG. 4B also shows a corresponding motion related frequency 460 (at approximately 50 beats per minute) and harmonics 470 of the motion related frequency. Because spectrograms 400 and 450 are substantially similar, conventional techniques may be unable to determine a heart rate (or other cardiovascular parameter). Specifically, FIGS. 4A and 4B depict a "heart rate equals cadence" scenario where a separate heart rate signal cannot be easily discerned using conventional techniques.

In FIG. 4A, the actual heart rate 430 of the subject is approximately 100 beats per minute, which coincides (or nearly coincides) with the second harmonic of the motion sensor signal. Therefore, conventional techniques may not be able to estimate a heart rate in instances where the heart rate coincides with the motion sensor signal or with one of its harmonics.

Some disclosed embodiments improve the accuracy and/or reliability of measured signals relating to one or more cardiovascular parameters from a biometric sensor. In some embodiments, robust cardiovascular parameter (e.g. heart rate) estimation using biometric sensors (e.g. optical, Photoplethysmograph (PPG), and/or ultrasonic sensors) coupled to a motion sensor (e.g. accelerometer, inertial measurement unit (IMU), gyroscopes etc) may be facilitated, in part, by using a physiological model to determine one or more cardiovascular parameters (e.g. a likely heart rate).

Figure 5A:
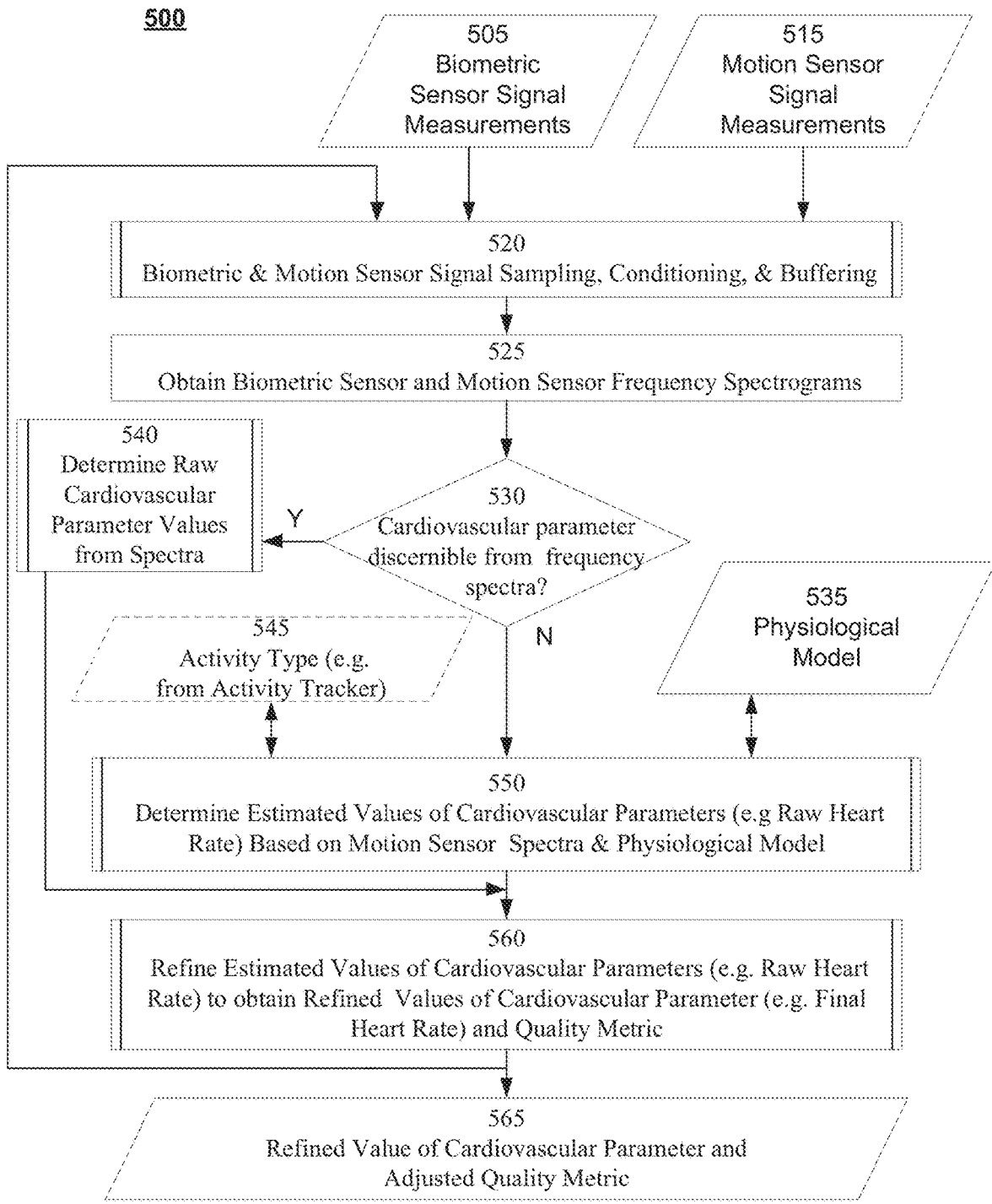
FIG. 5A shows a flowchart depicting an exemplary method of obtaining biometric information in accordance with some disclosed embodiments.

FIG. 5A shows a flowchart depicting an exemplary method 500 of obtaining biometric information (e.g. one or more cardiovascular parameters such heart rate) based on biometric and motion sensor signal measurements in accordance with some disclosed embodiments. In some embodiments, some or all of method 500 may be performed by device 100 (e.g. using one or more of processor(s) 150, biometric processor 155 and/or CPE processor 158) based, in part, on cardiovascular parameter measurements by biometric sensor 132 and measurements by motion sensor 136.

In some embodiments, in block 520, biometric and motion sensor signals may be sampled periodically to obtain biometric sensor signal measurements 505 and motion sensor signal measurements 515. In Biometric and Motion Sensor Signal Sampling, Conditioning and Buffering block 520, measured signal samples including biometric sensor signal measurements 505 and motion sensor signal measurements 515 may be conditioned (e.g. to remove outliers and noise artifacts) and buffered (e.g. stored in memory 160).

In block 525, a biometric (e.g. optical, PPG, ultrasonic etc.) sensor frequency spectrogram and a motion sensor (e.g. accelerometer) frequency spectrogram may be obtained. For example, the biometric sensor frequency spectrogram and a motion sensor frequency spectrogram may be obtained from the respective (biometric or motion sensor) buffered time domain signals using FFT or similar techniques.

For example, FFT may be performed on buffered and conditioned (a) biometric sensor measurement samples and (b) motion sensor measurement samples using a moving time window (e.g. a time interval of several seconds prior to the current time). In one embodiment, Fast Fourier Transform (FFT) based techniques may be used on the biometric and motion sensor input signal samples to obtain a frequency domain representation of the input signals. The magnitudes of the FFT of the input biometric and motion signals may be squared to obtain the corresponding power spectrum for each signal. Techniques other than simple FFT such as non-parametric methods such as Welch's method, or parametric methods, such as autoregressive model estimation, may be used to obtain the power spectrum of the conditioned biometric and motion sensor signals in the input buffer. In some embodiments, parameters (such as frequencies, signal power etc) associated with the power spectra data may be timestamped and recorded.

In block 530, if biometric sensor signals in biometric sensor spectrogram are not obscured by motion ("Y" in block 530) then, in block 550, the one or more cardiovascular parameters (e.g. a raw heart rate) may be determined based on the biometric sensor spectrogram. In block 550, the one or more cardiovascular parameters (e.g. a raw heart rate) may be determined from a comparison of the motion sensor frequency spectrum and the biometric sensor frequency spectrum using any known technique. For example, a frequency in the biometric spectrogram that is not present in the motion sensor spectrogram and satisfies other signal and/or quality parameters may be selected as a raw heart rate. Block 560 may then be invoked.

In some embodiments, in block 550, a fundamental frequency associated with a cardiovascular parameter in the biometric sensor signal may be determined by: removing frequencies associated with the frequency domain representation of the motion sensor signal from the frequency domain representation of the biometric sensor signal. The fundamental frequency associated with associated with the cardiovascular parameter in the biometric sensor signal may then be determined from frequencies remaining in the frequency domain representation of the biometric sensor signal (i.e. after removal of frequencies associated with the frequency domain representation of the motion sensor signal).

For example, frequencies identified in the motion sensor spectrogram may be removed from the biometric sensor spectrogram as outlined previously. Further, a set of frequencies (e.g. harmonics) associated with a fundamental frequency in biometric sensor spectrogram may be determined and the fundamental frequency may be identified. In some embodiments, estimated values of cardiovascular parameters (e.g. a raw heart rate) may be determined based on a corresponding fundamental frequency in the biometric sensor spectrogram.

In block 530, when a fundamental frequency associated with a cardiovascular parameter is not discernible from a comparison of the biometric and motion sensor spectrograms ("N" in block 530) then, in block 550, estimated values for one or more cardiovascular parameters (e.g. raw heart rate) may be determined based on biometric and motion sensor spectra and input provided by physiological model 535. For example, in block 530, a heart rate may not be easily determinable from the biometric sensor frequency spectrogram in a heart rate equal cadence scenario or when biometric sensor signals in biometric sensor spectrogram are obscured by motion.

In some embodiments, in block 550, if one or more cardiovascular parameters cannot be determined from a comparison of the motion sensor frequency spectrum and the biometric sensor frequency spectrum, then an activity type may be determined based on the frequency domain representation of the motion sensor signal. In some embodiments, based on the determined activity type, physiological model 535 may provide a corresponding likely value for each of the one or more cardiovascular parameters. For example, based on the activity type, physiological model 535 may provide information related to the one or more cardiovascular parameters including one or more of: a likely value for the cardiovascular parameters (e.g. a likely heart rate) and/or cardiovascular parameter statistics (e.g. maximum, minimum, average, median, or mode, standard deviation, variance etc for the cardiovascular parameters—such as heart rate).

In some embodiments, when identifying an activity based on a motion related signal or a cardiovascular or heart rate related signal, spectral frequency content may be examined for patterns of multiples of a fundamental frequency. For example, referring to FIGS. 3A and 3B, these sets of harmonics are: (a) fundamental frequency 310 and its harmonics 320 (in FIG. 3A); and (b) fundamental frequency 360 and its harmonics 370 (in FIG. 3B), respectively. In FIGS. 4A and 4B, the sets of harmonics are shown as: (a) fundamental frequency 410 and its harmonics 420 (in FIG. 3A); and fundamental frequency 460 and its harmonics 470 (in FIG. 3B), respectively.

In some embodiments, all spectral frequency peaks, at any one time, may be examined to see if they fall into a set of harmonics. In some embodiments, to determine an activity type, signals in a set of harmonics may be combined to obtain a measure of power in the corresponding set of harmonics and identify the strongest repeating signals. The signals from multiple spectral peaks may be combined using one or more of the following methods: the spectral peak values may be added; the integrated signal in the spectral peaks may be added; the number of spectral peaks in the set may be counted; and/or the width of individual peaks within the set of harmonics may be combined or averaged. In some embodiments, a temporal rate of change of spectral peak locations in the set of harmonics may be used along with one or more metrics above to determine an activity type. The temporal rate of change of spectral peak locations in the set of harmonics may provide an indication of changes in the intensity of the activity.

The spectral peaks may be obtained as the power in the signal, the amplitude of the signal, or in some other functional form. Once a value representing a measure of power is determined for a set of harmonics, the measure of power may be compared with the corresponding measures of power for other sets of harmonics to determine the strongest set and/or compared against thresholds. In some embodiments, empirical data may be used to determine power thresholds that separate activity types. For example, the empirical data may be obtained from multiple users (e.g. from a population sample), may be user-specific, or a combination thereof. In some embodiments, input pertaining to the location of device 100 and/or motion sensor 136 on a subject (e.g. arm, shoulder, wrist, chest, ankle, head etc) may be used to inform threshold selection. For example, different thresholds may be used for a given activity based on the location of device 100 and/or motion sensor 136 on a subject.

In some embodiments, a user profile may also be used to determine power thresholds that separate activity types. For example, device 100 may request input (e.g. a confirmation of a determined activity type or input of the activity type) from a user when the user performs an activity type. In some embodiments, power thresholds that are both user-specific and activity-specific may be determined based on aggregated measurements for the user for each activity type. In some embodiments, the user-specific and activity-specific power thresholds may further be varied based on the location of device 100 and/or motion sensor 136 on a subject. For example, the location of device 100 and/or motion sensor 136 on a subject may be determined from a user-profile or a user-input.

In some embodiments, the measure of power associated with the strongest set of harmonics may be used to determine an activity type. In some embodiments, activity types may be correlated with measures of power. Thus, when a measure of power is known an activity type may be determined. In some embodiments, the correlation may be user-specific.

Referring to FIG. 5A, in some embodiments, the activity type may be provided to physiological model 535.

Figure 5B:
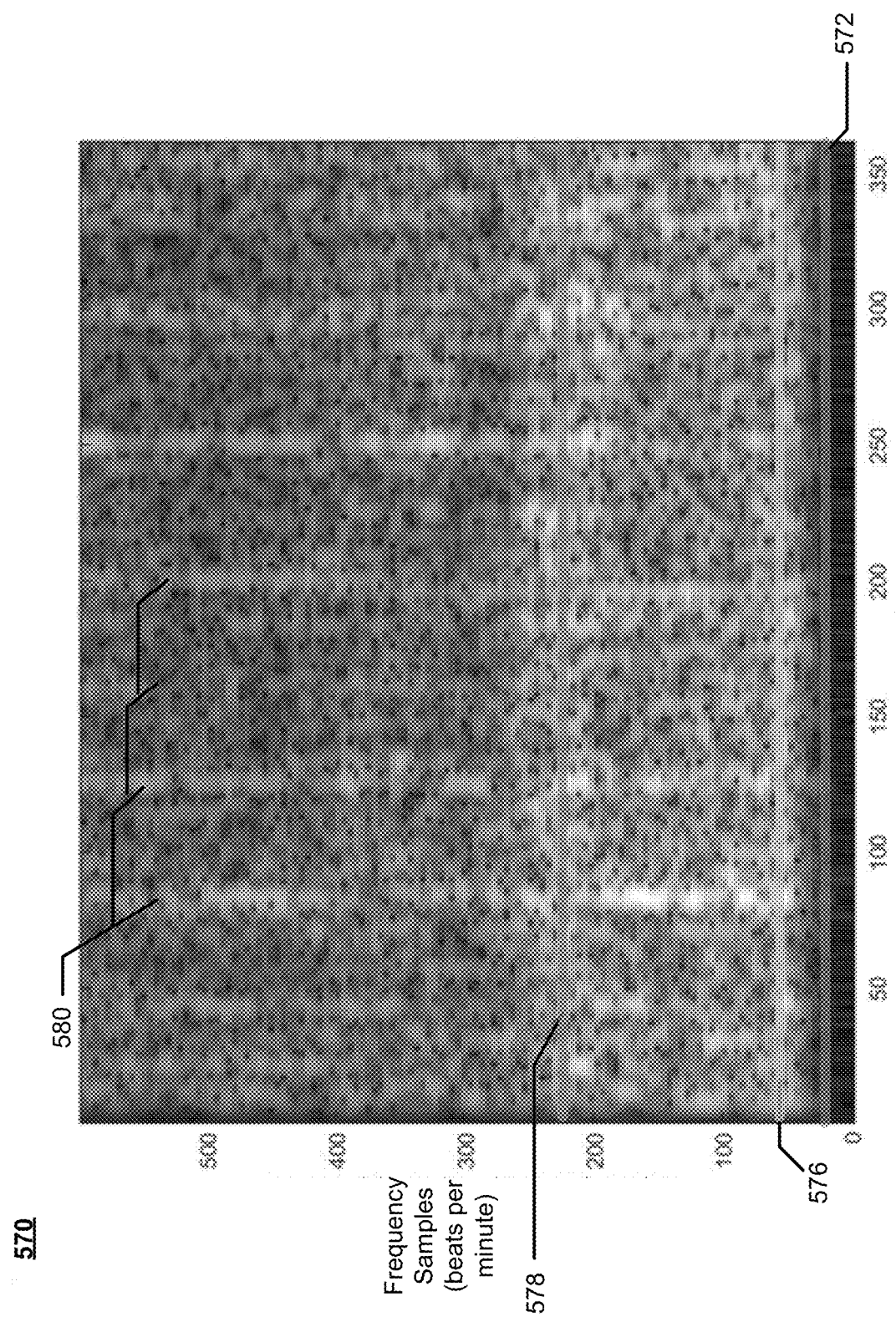
FIG. 5B shows an exemplary accelerometer spectral pattern from a bicycling activity.

FIG. 5B shows exemplary accelerometer spectral pattern 570 from bicycling, In FIG. 5B, spectral response 570 shows motion from a wrist worn accelerometer for bicycling (activity type). The horizontal axis shows time in seconds and the vertical axis shown the temporal frequency in cycles per minute. The intensity of the plot represents the power at that frequency and time. Spectral response 570 shows the broad spectrum of vibrations ranging from a low 572 of around 20 cycle/minute and more intense frequency bands 576 near 50 cycle/minute as well as more intense frequency bands 578 around 220 cycle/minute. The vertical bands 580 correspond to strong and sudden motion of the accelerometer. In some embodiments, based on the spectral power and/or the periodic strong surges of motion, an activity type (e.g. bicycling) may be determined. In some embodiments, the spectral power in the motion sensor signal may be correlated with an activity type. For example, based on the value of the integrated power in the motion sensor signal, activity type 545 may be inferred. Thus, parameters in the spectral pattern in FIG. 5B, and/or parameters derived from the spectral pattern in FIG. 5B, may be used to determine a bicycling activity type. In some embodiments, an activity type may be determined from an analysis of motion sensor signals based on signatures or patterns associated with the motion sensor signals (e.g. as outlined above for bicycling).

In some embodiments, a cumulative probability distribution function of a classifier metric may be used determine a likely activity type. The value of cumulative distribution function (cdf) is the probability that a corresponding continuous random variable (e.g. the classifier metric X) has a value less than or equal to the argument of the function. Mathematically, this may be expressed as $F(x)=P(X \leq x)$.

Figure 5C:
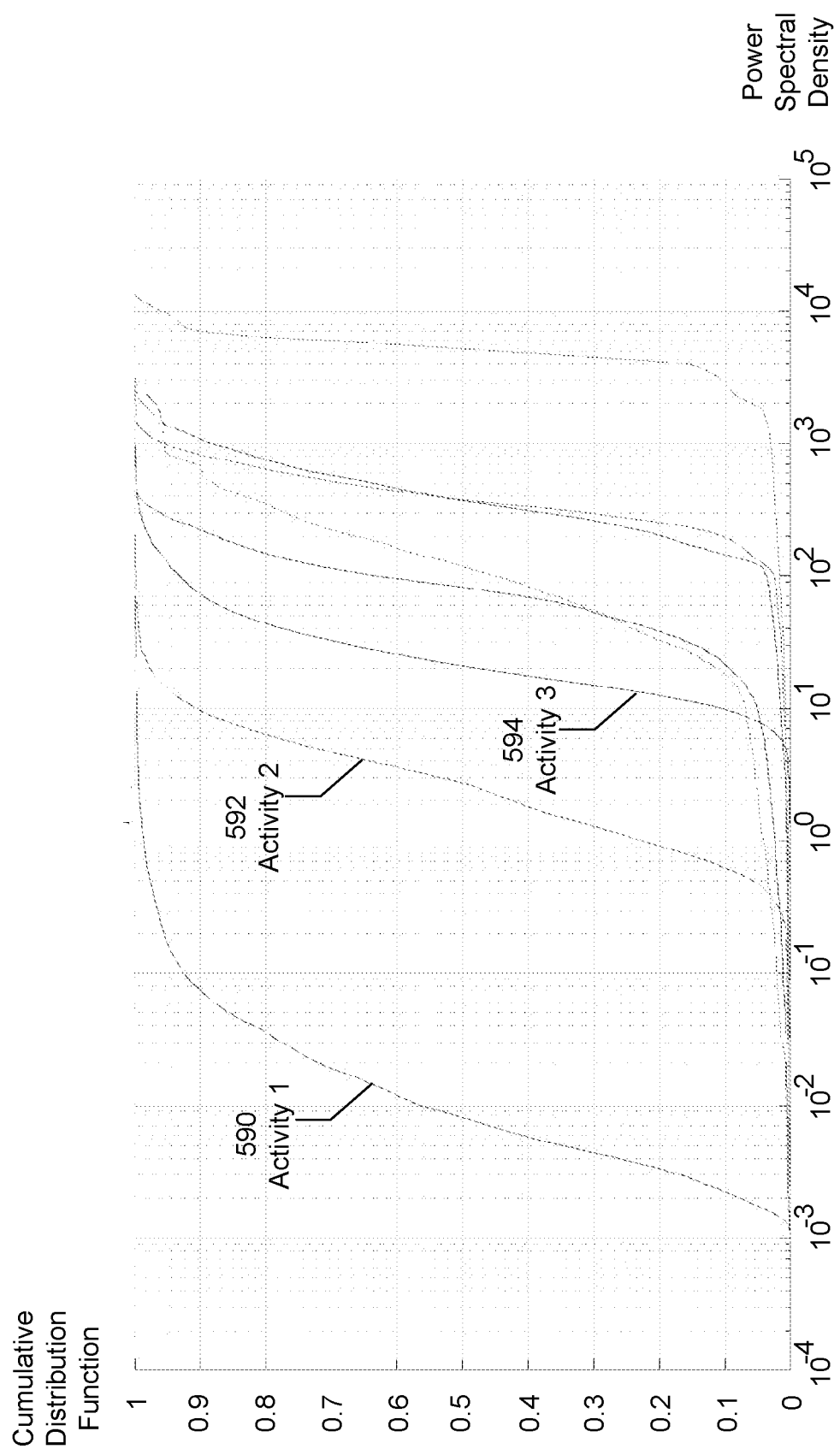
FIG. 5C shows a plot of the power spectral density against the cumulative probability distribution for various activity types.

FIG. 5C shows a plot of the power spectral density (the classifier metric) against the cumulative probability distribution for various activity types. In FIG. 5C, each curve corresponds to a distinct activity type. As shown in FIG. 5C, the plots of the power spectrum distribution against the cdf for Activity 1 590, Activity 2 592, and Activity 3 594 are spread over different regions of the graph. Accordingly, by setting appropriate thresholds for the values of the power spectrum distribution, activity types may be differentiated.

Referring to FIG. 5A, in some embodiments, an activity type 545 may be provided by an activity tracker (e.g. a device communicatively coupled to device 100; or an application running on or communicatively coupled to device 100). Activity type 545 may be provided to physiological model 535, which may, based on the activity type 545, provide one or more cardiovascular parameters including one or more of: a likely heart rate, heart rate statistics (e.g. maximum, minimum, average, median, or mode, standard deviation, variance), heart rates based on elapsed time since the start of the activity and other measures.

In some embodiments, physiological model 535 may provide likely cardiovascular parameter values for the cardiovascular parameters (e.g. a likely heart rate), which may be: (a) user-specific, (b) activity specific or (c) both user-specific and activity-specific. Further, because cardiovascular parameters may vary based on the length of time that a user indulges in an activity, in some embodiments, the likely values of the cardiovascular parameters and/or cardiovascular parameter statistics may be correlated with elapsed time from start of the activity when the start time is known or can be determined (e.g. based on measurements by the motion sensor 136, or input from an activity tracker, or user-input).

In some embodiments, physiological model 535 may include user-specific information such as a minimum or maximum heart rate, average heart rate, which may further be classified by activity type and/or correlated with time from start of the activity, age, gender, history of exercise, maximal oxygen consumption ($VO_2$ max) for the user. In some embodiments, when user-specific information is unavailable (e.g. when there are no prior recorded measurements), default values (e.g. obtained from a general population sample) for cardiovascular parameters (e.g. heart rate) for the activity type may be used. The default values may be augmented and/or replaced with user-specific information as information is captured based on motion sensor (or activity tracker) measurements. In some embodiments, available user-specific information may be used to obtain more tailored default values. For example, when the age of the user is known (but no user-specific activity history is available), the default likely values and/or statistics of the cardiovascular parameters for the activity type may be age-specific. As another example, when $VO_2$ max is known or available, the default likely values and/or statistics of the cardiovascular parameters for the activity type may be based on the values of $VO_2$ max.

In some embodiments, in block 550, estimated values for the one or more cardiovascular parameters (e.g. a raw heart rate) may be determined based, in part, on the likely values of the one or more cardiovascular parameters (e.g. likely heart rate), which may be provided by physiological model 535. In some embodiments, in block 550, for each cardiovascular parameter, a corresponding fundamental frequency in the biometric sensor signal may be determined based on frequencies present in the frequency domain representation of the motion sensor signal. For example, the likely values of the one or more cardiovascular parameters (e.g. provided by the physiological model) may each be correlated with a corresponding frequency. In some embodiments, the fundamental frequency associated with a cardiovascular parameter in the biometric sensor signal may be determined from frequencies present in the frequency domain representation of the motion sensor signal that are proximate (e.g. using some statistical measure) to the frequency associated with the corresponding likely value of the cardiovascular parameter.

For example, the likely value of the cardiovascular parameter (e.g. likely heart rate) and statistical parameters (e.g. an average heart rate and a standard deviation) related to a cardiovascular parameter (e.g. heart rate) may be correlated with a first frequency $f_1$. Frequency $f_1$ may be used to narrow the search space in the frequency domain representation of the motion sensor signal. For example, a frequency $f_2$ that is proximate (by some statistical measure) to frequency $f_1$ in the frequency domain representation of the motion sensor signal may be determined to be the fundamental frequency associated with the cardiovascular parameter in the biometric sensor signal. An estimated value of the cardiovascular parameter (e.g. a raw heart rate) may then be determined based on the frequency $f_2$ in frequency domain representation of the motion sensor signal. In the example above (heart rate equal cadence), as one possibility, a frequency $f_2$ present in the frequency spectrogram of the motion sensor that is closest to frequency $f_1$ may be determined to be the fundamental frequency associated with the cardiovascular parameter in the biometric sensor signal. As another example, when heart rate equal cadence occurs, a frequency $f_2$ present in the frequency spectrogram of the motion sensor that falls within some interval (e.g. one standard deviation) of the frequency $f_1$ may be determined to be the fundamental frequency associated with a cardiovascular parameter in the biometric sensor signal. In some embodiments, frequency $f_1$ may be directly selected as the fundamental frequency associated with a cardiovascular parameter in the biometric sensor signal (i.e. frequency $f_2$ may be set equal to frequency $f_1$ ($f_2=f_1$)).

As outlined above, an estimated value of the cardiovascular parameter (e.g. a raw heart rate) may then be determined based on the frequency $f_2$ in frequency domain representation of the motion sensor signal. In some embodiments, the likely heart rate (e.g. provided by physiological model 535) may be directly used as the raw heart rate. In some embodiments, one of the average, mode, or median or likely heart rate (as provided by the physiological model 535) may be selected as the raw heart rate.

In block 560, the one or more estimated cardiovascular parameters (e.g. raw heart rate) may be refined based on other signal measurements/parameters to obtain a refined estimate of the cardiovascular parameters (e.g. a final heart rate) and a quality metric 565. The quality metric may provide an indication of the reliability of the refined estimate of the cardiovascular parameters (e.g. final heart rate). For example, a higher quality metric may be used when the one or more cardiovascular parameters (e.g. a heart rate) is discernible from a comparison of the motion sensor and biometric sensor frequency spectrograms. As another example, the quality metric may be adjusted based on how closely the final frequency of the cardiovascular parameters (e.g. final heart rate) corresponds to the likely frequency of the cardiovascular parameters (e.g. heart rate) predicted by the physiological model. As a further example, the quality metric may reflect the confidence (or likelihood) of the activity type input from the activity tracker and/or predicted or inferred based on motion sensor signals. In some embodiments, the quality metrics may be based on a signal to noise ratio (SNR). For example, the ratio of the magnitude of the biometric signal (signal) to the magnitude of the motion signal (noise) may be used, at least in part, to derive a quality metric.

In some embodiments, another iteration of method 500 may then commence from step 520.

Figure 6:
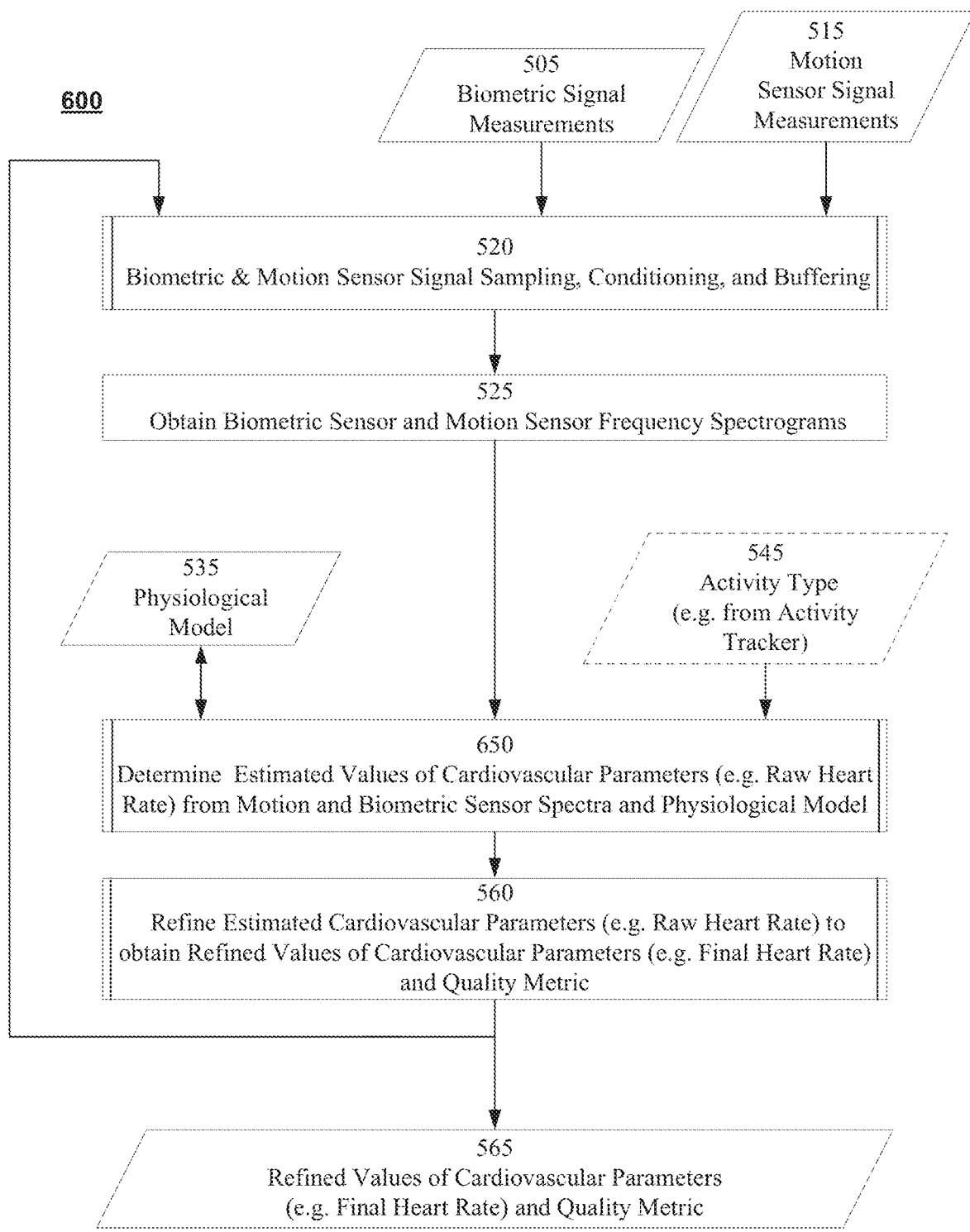
FIG. 6 shows a flowchart depicting an exemplary method of obtaining biometric information in accordance with some disclosed embodiments.

FIG. 6 shows a flowchart depicting an exemplary method 600 of obtaining biometric information (e.g. one or more cardiovascular parameters such as heart rate) based on biometric and motion sensor signal measurements in accordance with some disclosed embodiments. In some embodiments, some or all of method 600 may be performed by device 100 (e.g. using one or more of processor(s) 150, biometric processor 155 and/or CPE processor 158) based, in part, on cardiovascular parameter measurements received from biometric sensor 132 and measurements by motion sensor 136.

In some embodiments, in block 520, biometric and motion sensor signals may be sampled periodically to obtain biometric sensor signal measurements 505 and motion sensor signal measurements 515. In Biometric and Motion Sensor Signal Sampling, Conditioning, and Buffering block 520, measured signal samples including biometric sensor signal measurements 505 and motion sensor signal measurements 515 may be conditioned (e.g. to remove outliers and noise artifacts) and buffered (e.g. stored in memory 160).

In block 525, a biometric (e.g. optical, PPG, ultrasonic, etc) sensor frequency spectrogram and a motion sensor (e.g. accelerometer) frequency spectrogram may be obtained. For example, the biometric sensor frequency spectrogram and a motion sensor frequency spectrogram may be obtained from the corresponding respective (biometric or motion sensor) buffered time domain signals using FFT or similar techniques.

For example, FFT may be performed on buffered and conditioned (a) biometric sensor measurement samples and (b) motion sensor measurement samples using a moving time window (e.g. a time interval of several seconds prior to the current time). In one embodiment, Fast Fourier Transform (FFT) based techniques may be used on the biometric and motion sensor input signal samples to obtain a frequency domain representation of the input signals. The magnitudes of the FFT of the input biometric and motion signals may be squared to obtain the corresponding power spectrum for each signal. Techniques other than simple FFT such as non-parametric methods such as Welch's method, or parametric methods, such as autoregressive model estimation, may be used to obtain the power spectrum of the conditioned biometric and motion sensor signals in the input buffer. In some embodiments, parameters (such as frequencies, signal power etc) associated with the power spectra data may be timestamped and recorded.

In block 650, estimated values for one or more cardiovascular parameters (e.g. a raw heart rate) may be determined based on the biometric sensor frequency spectrogram, motion sensor frequency spectrogram, and input provided by physiological model 535.

For example, when biometric sensor signals in biometric sensor spectrogram are not obscured by motion then, in block 650, the one or more cardiovascular parameters (e.g. a raw heart rate) may be determined based on the biometric sensor spectrogram. When biometric sensor signals are not obscured by motion, the one or more cardiovascular parameters (e.g. a raw heart rate) may be determined from a comparison of the motion sensor frequency spectrum and the biometric sensor frequency spectrum using any known technique. For example, a frequency in the biometric spectrogram that is not present in the motion sensor spectrogram and satisfies other signal and/or quality parameters may be selected as a raw heart rate. Block 560 may then be invoked.

In some embodiments, in block 650, a fundamental frequency associated with a cardiovascular parameter in the biometric sensor signal may be determined by: removing frequencies associated with the frequency domain representation of the motion sensor signal from the frequency domain representation of the biometric sensor signal. The fundamental frequency associated with associated with the cardiovascular parameter in the biometric sensor signal may then be determined from frequencies remaining in the frequency domain representation of the biometric sensor signal (i.e. after removal of frequencies associated with the frequency domain representation of the motion sensor signal).

In some embodiments, in block 650, for each cardiovascular parameter, the corresponding fundamental frequency in the biometric sensor signal may be determined based on frequencies present in the frequency domain representation of the motion sensor signal (e.g. in instances where heart rate equal cadence occurs). For example, a heart rate may not be easily determinable from the biometric sensor frequency spectrogram in a heart rate equal cadence scenario or when biometric sensor signals in biometric sensor spectrogram are obscured by motion.

In some embodiments, in block 650, when a fundamental frequency associated with a cardiovascular parameter is not discernible from a comparison of the biometric and motion sensor spectrograms, then, an activity type may be determined based on the frequency domain representation of the motion sensor signal. In some embodiments, based on the determined activity type, physiological model 535 may provide a corresponding likely value for each of the one or more cardiovascular parameters. For example, physiological model 535 may provide information related to the one or more cardiovascular parameters including one or more of: a likely value for the cardiovascular parameters (e.g. a likely heart rate) and/or cardiovascular parameter statistics (e.g. maximum, minimum, average, median, or mode, standard deviation, variance etc for the cardiovascular parameters—such as heart rate).

In some embodiments, to determine an activity type, signals in a set of harmonics may be combined to obtain a measure of power in the set of harmonics and identify the strongest repeating signals. The signals from multiple spectral peaks may be combined in a variety of methods: the spectral peak values may be added, the integrated signal in the spectral peaks may be added, the number of spectral peaks in the set may be counted; and/or the width of individual peaks within the set of harmonics may be combined or averaged. The spectral peaks may be obtained as the power in the signal, the amplitude of the signal, or some other functional form.

In some embodiments, the measure of power associated with the strongest (highest measure of power) set of harmonics may be used to determine an activity type. Once a value for the measure of power is determined for a set of harmonics, the measure of power may be compared with the corresponding measures of power for other sets of harmonics to determine the strongest set and/or compared against a threshold to identify an activity type. In some embodiments, one or more threshold values (which may be determined empirically) may be associated with each activity type. For example, for each activity type, the corresponding power spectral density may be plotted against the cdf to determine appropriate thresholds for the activity type.

In some embodiments, the spectral power in the motion sensor signal may be correlated with an activity type. For example, based on the value of the integrated power in the motion sensor signal, activity type 545 may be inferred. In some embodiments, a spectral pattern (e.g. as in FIG. 5B) and/or parameters derived from the spectral pattern, may be used to determine activity type 545 (e.g. bicycling). In some embodiments, an activity type may be determined from an analysis of motion sensor signals based on a signature or pattern associated with the motion sensor signals (e.g. as outlined above for bicycling). In some embodiments, activity types may be correlated with measures of power. In some embodiments, the correlation may be user-specific. In some embodiments, the activity type may be provided to physiological model 535.

In some embodiments, a temporal rate of change of spectral peak locations in the set of harmonics may be used along with one or more metrics above to determine an activity type. The temporal rate of change of spectral peak locations in the set of harmonics may provide an indication of changes in the intensity of the activity.

In some embodiments, physiological model 535 may provide likely cardiovascular parameter values for the cardiovascular parameters (e.g. a likely heart rate), which may be: (a) user-specific, (b) activity specific or (c) both user-specific and activity-specific. Further, in some embodiments, the likely values of the cardiovascular parameters and/or cardiovascular parameter statistics may be correlated with elapsed time from start of the activity when the start time is known or can be determined.

In some embodiments, as outlined above, physiological model 535 may include user specific information such as a minimum or maximum heart rate, average heart rate, which may further be classified by activity type and/or correlated with time from start of the activity, age, gender, history of exercise, maximal oxygen consumption ($VO_2$ max) for the user. In some embodiments, when user-specific information is unavailable (e.g. when there are no prior recorded measurements), default values (e.g. obtained from a general population sample) for cardiovascular parameters (e.g. heart rate) for the activity type may be used. The default values may be augmented and/or replaced with user-specific information as information is captured based on motion sensor (or activity tracker) measurements. In some embodiments, available user-specific information may be used to obtain more tailored default values as outlined previously.

In some embodiments, in block 650, estimated values for the one or more cardiovascular parameters (e.g. a raw heart rate) may be determined based, in part, on the likely values of the one or more cardiovascular parameters (e.g. likely heart rate), which may be provided by physiological model 535. In some embodiments, in block 650, for each cardiovascular parameter, a corresponding fundamental frequency in the biometric sensor signal may be determined based on frequencies present in the frequency domain representation of the motion sensor signal. For example, the likely values of the one or more cardiovascular parameters (e.g. provided by the physiological model) may each be correlated with a corresponding frequency. In some embodiments, the fundamental frequency associated with a cardiovascular parameter in the biometric sensor signal may be determined from frequencies present in the frequency domain representation of the motion sensor signal that are proximate (e.g. using some statistical measure) to the frequency associated with the corresponding likely value of the cardiovascular parameter.

For example, the likely value of the cardiovascular parameter (e.g. likely heart rate) and statistical parameters (e.g. an average heart rate and a standard deviation) related to a cardiovascular parameter (e.g. heart rate) may be correlated with a first frequency $f_1$. Frequency $f_1$ may be used to narrow the search space in the frequency domain representation of the motion sensor signal. For example, a frequency $f_2$ that is proximate (by some statistical measure) to frequency $f_1$ in the frequency domain representation of the motion sensor signal may be determined to be the he fundamental frequency associated with the cardiovascular parameter in the biometric sensor signal. An estimated value of the cardiovascular parameter (e.g. a raw heart rate) may then be determined based on the frequency $f_2$ in frequency domain representation of the motion sensor signal. As one possibility, when heart rate equal cadence occurs, a frequency $f_2$ present in the frequency spectrogram of the motion sensor that is closest (e.g. minimum absolute difference) to frequency $f_1$ may be determined to be the fundamental frequency associated with the cardiovascular parameter in the biometric sensor signal. As another example, when heart rate equal cadence occurs, a frequency $f_2$ present in the frequency spectrogram of the motion sensor that falls within some interval (e.g. one standard deviation) of the frequency $f_1$ may be determined to be the fundamental frequency associated with a cardiovascular parameter in the biometric sensor signal. In some embodiments, frequency $f_1$ may be selected as the fundamental frequency associated with a cardiovascular parameter in the biometric sensor signal (i.e. frequency $f_2$ may be set equal to frequency $f_1$ ($f_2=f_1$)).

As outlined above, an estimated value of the cardiovascular parameter (e.g. a raw heart rate) may then be determined based on the frequency $f_2$ in frequency domain representation of the motion sensor signal. In some embodiments, the likely heart rate (e.g. provided by physiological model 535) may be used as the raw heart rate. In some embodiments, one of the average, mode, or median or likely heart rate (as provided by the physiological model 535) may be selected as the raw heart rate.

In block 560, the one or more estimated cardiovascular parameters (e.g. raw heart rate) may be refined based on other signal measurements/parameters to obtain a refined estimate of the cardiovascular parameters (e.g. a final heart rate) and a quality metric 565. The quality metric may provide an indication of the reliability of the refined estimate of the cardiovascular parameters (e.g. final heart rate). For example, a higher quality metric may be used when the one or more cardiovascular parameters (e.g. a heart rate) is discernible from a comparison of the motion sensor and biometric sensor frequency spectrograms. As another example, the quality metric may be adjusted based on how closely the final frequency of the cardiovascular parameters (e.g. final heart rate) corresponds to the likely frequency of the cardiovascular parameters (e.g. heart rate) predicted by the physiological model. As a further example, the quality metric may reflect the confidence (or likelihood) of the activity type input from the activity tracker and/or predicted or inferred based on motion sensor signals. In some embodiments, the quality metrics may be based on a signal to noise ratio (SNR). For example, the ratio of the magnitude of the biometric signal (signal) to the magnitude of the motion signal (noise) may be used, at least in part, to derive a quality metric.

In some embodiments, another iteration of method 600 may then commence from step 520.

Figure 7:
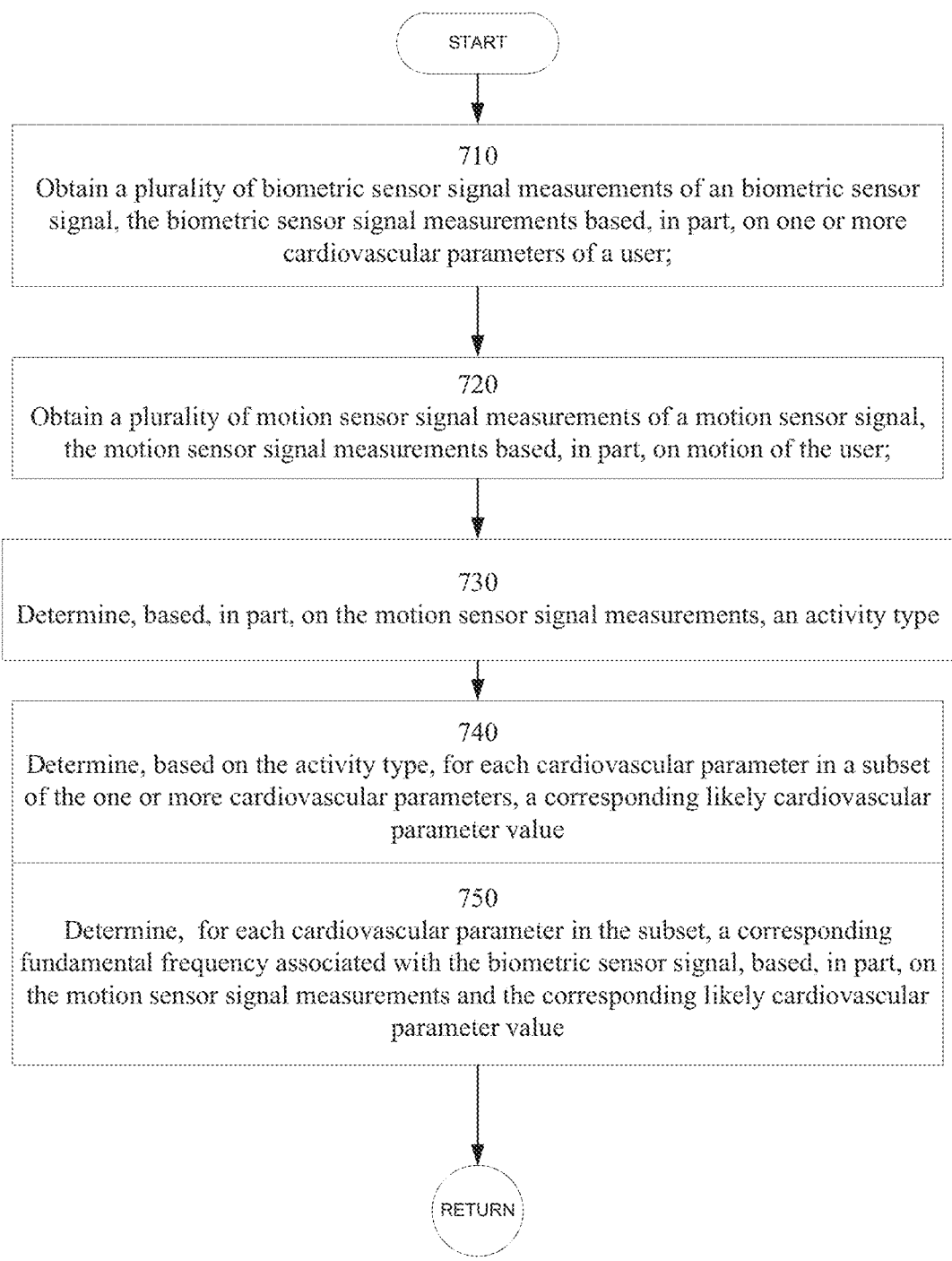
FIG. 7 shows a flowchart depicting an exemplary method of obtaining biometric information such as heart rate based on biometric and motion sensor signal measurements in accordance with some disclosed embodiments.

FIG. 7 shows a flowchart depicting an exemplary method 700 of obtaining determining a cardiovascular parameter (such as a heart rate) based on biometric and motion sensor signal measurements in accordance with some disclosed embodiments. In some embodiments, the method 700 may be performed on device 100, which may be at least one of: a wearable device; or a mobile device; or a wearable device coupled to a mobile device. In some embodiments, method 700 may be performed by processor(s) 150, biometric processor 155 and/or CPE processor 158. In some embodiments, some or all of method 700 may be performed by device 100 using one or more of processor(s) 150, biometric processor 155 and/or CPE processor 158 based, in part, on cardiovascular parameter measurements received from biometric sensor 132, and measurements by motion sensor 136.

In block 710, a plurality of biometric sensor signal measurements of a biometric sensor signal may be obtained, where the biometric sensor signal measurements may be based, in part, on one or more cardiovascular parameters of a user. For example, biometric sensor signal measurements may be obtained from biometric sensor 132, which may measure blood flow volume of the user. For example, the biometric sensor signal measurements may comprise optical sensor or Photoplethysmographic (PPG) sensor, or ultrasonic sensor measurements.

In some embodiments, FFT may be performed on buffered and conditioned biometric sensor measurement samples using a moving time window (e.g. a time interval of several seconds prior to the current time). In one embodiment, Fast Fourier Transform (FFT) based techniques may be used on the biometric sensor input signal samples to obtain a frequency domain representation of the input signals. The magnitudes of the FFT of the input biometric signals may be squared to obtain the corresponding biometric power spectrum for each signal.

In block 720, a plurality of motion sensor signal measurements of a motion sensor signal may be obtained, where the motion sensor signal measurements may be based, in part, on motion of the user. For example, motion sensor signal measurements may be obtained from motion sensor 136, which may measure parameters related to user motion. For example, the motion sensor signal measurements comprise at least one of: accelerometer measurements; or Inertial Measurement Unit (IMU) measurements.

In some embodiments, FFT may be performed on buffered and conditioned motion sensor measurement samples using a moving time window (e.g. a time interval of several seconds prior to the current time). In one embodiment, Fast Fourier Transform (FFT) based techniques may be used on the motion sensor input signal samples to obtain a frequency domain representation of the input signals. The magnitudes of the FFT of the input motion sensor signals may be squared to obtain the corresponding motion sensor power spectrum for each signal.

In block 730, an activity type may be determined based on the motion sensor measurements. In some embodiments, an activity type may be determined based on the motion sensor measurements when non-motion related frequencies are not discernible in a frequency domain representation of the biometric sensor signal. For example, an activity type may be determined based on the motion sensor measurement, when a fundamental frequency associated with the biometric sensor signal cannot be determined from the frequency domain representation of the biometric sensor signal.

In some embodiments, in block 730, the activity type may be determined from an analysis of motion sensor signal. For example, a signature or pattern associated with the motion sensor signals may be used to determine an activity type.

In some embodiments, to determine an activity type (e.g. biking, rowing, running, etc) signals in a set of harmonics may be combined to identify the strong repeating signals. The signals from multiple spectral peaks may be combined in a variety of methods: the spectral peak values may be added, the integrated signal in the spectral peaks may be added, the number of spectral peaks in the set may be counted; and/or the width of individual peaks within the set of harmonics may be combined or averaged.

In some embodiments, to determine an activity type associated with the motion of the user: a spectral power in the motion sensor signal may be determined (e.g. as outlined above), and the activity type may be determined based on the spectral power. For example, the spectral power in the motion sensor signal may be determined by: obtaining a spectral power value based, in part, on a first set of harmonics in a frequency domain representation of the motion sensor signal; and determining the activity type based on the spectral power value. The spectral power value may be obtained by: determining a plurality of second sets of harmonics in the frequency domain representation of the motion sensor signal; obtaining, corresponding to each second set of harmonics, a corresponding power measure; comparing the corresponding power measures for the plurality of second sets of harmonics; and selecting, based on the comparison, the first set of harmonics from the plurality of second sets of harmonics. For example, a specific second set of harmonics with a highest power measure relative to other second sets of harmonics (in the plurality of second sets of harmonics) may be selected as the first set of harmonics.

For each second set of harmonics, the corresponding power measure may be obtained by one of: obtaining the corresponding power measure based on a count of a number of spectral peaks in the second set of harmonics; or obtaining the corresponding power measure based on a sum of amplitudes of spectral peaks in the second set of harmonics; or obtaining the corresponding power measure based on a sum of integrated spectral peak signals in the second set of harmonics.

In some embodiments, the corresponding power measures for the plurality of second sets of harmonics may be compared by one of: comparing the corresponding power measures for the plurality of second sets of harmonics to each other; or comparing the corresponding power measures for plurality of second sets of harmonics to a threshold. In some embodiments, plots of the power spectrum distribution against the cdf for each activity type (e.g. as shown in FIG. 5C) may be used to determine appropriate thresholds (e.g. using empirical data during device calibration or device configuration).

In some embodiments, a temporal rate of change of spectral peak locations in the set of harmonics may be used along with one or more metrics above to determine an activity type. The temporal rate of change of spectral peak locations in the set of harmonics may provide an indication of changes in the intensity of the activity etc. The spectral peaks may be obtained as the power in the signal, the amplitude of the signal, or some other functional form. Once a value is assigned to a combination of harmonic values, the value may be compared with other sets, and/or compared against a threshold to identify an activity type.

In some embodiments, the spectral power in the motion sensor signal may be correlated with an activity type. In some embodiments, an activity type may, alternatively or additionally, be provided by an activity tracker (e.g. an application. running on device 100 or a device communicatively coupled to device 100) and/or determined from an analysis of motion sensor signals (e.g. a signature or pattern associated with the motion sensor signals).

In block 740, based on the activity type, a likely value for the cardiovascular parameter may be determined. In some embodiments, the one or more cardiovascular parameters may comprise a heart rate and the corresponding likely cardiovascular parameter value may comprise a likely heart rate. In some embodiments, the corresponding likely cardiovascular parameter value for each cardiovascular parameter in the subset may be determined by using a physiological model, wherein, for each cardiovascular parameter in the subset, the physiological model correlates the activity type with the corresponding likely cardiovascular parameter value. In some embodiments, the activity type with the corresponding likely cardiovascular parameter value is user-specific.

In some embodiments, the physiological model (e.g. physiological model 535) may provide information related to the one or more cardiovascular parameters including one or more of: a likely value for the cardiovascular parameter (e.g. a likely heart rate) and/or cardiovascular parameter statistics. The physiological model may be selected based on at least one of: motion signal parameters, patterns in the motion sensor signal, and/or an activity type provided by an activity tracker and/or user-input. In some embodiments, the physiological model may provide a likely value for at least one cardiovascular parameter (e.g. a likely heart rate), which may be: (a) user-specific, (b) activity specific or (c) both user-specific and activity-specific. Further, the likely values of the cardiovascular parameters and/or cardiovascular parameter statistics may be correlated with elapsed time from start of the activity, when the start time is known or can be determined (e.g. based on measurements by the motion sensor 136, or input from an activity tracker, or user-input). In some embodiments, physiological model 535 may include user specific information such as a minimum or maximum heart rate, average heart rate, which may further be classified by activity type and/or correlated with time from start of the activity, age, gender, history of exercise, maximal oxygen consumption ($VO_2$ max) for the user. In some embodiments, when user-specific information is unavailable (e.g. when there are no prior recorded measurements), default values (e.g. obtained from a general population sample) for cardiovascular parameters (e.g. heart rate) for the activity type may be used.

In block, 750, a fundamental frequency associated with the biometric sensor signal may be determined, based, in part, on the at least one likely value of the cardiovascular parameter and the motion sensor signal measurements (e.g. from motion sensor 136). The at least one likely value of the cardiovascular parameter may be correlated with and/or used to determine at least one frequency corresponding to the at least one likely value of the cardiovascular parameter. In some embodiments, in block 750, the fundamental frequency associated with the biometric sensor signal may be determined based on frequencies present in the frequency domain representation of the motion sensor signal that are proximate to the at least one frequency corresponding to the likely value of the cardiovascular parameter.

For example, the at least one likely value of the cardiovascular parameter may include a likely value (e.g. a likely heart rate) and/or statistical parameters such as an average and a standard deviation (e.g. average heart rate and standard deviation) related to the cardiovascular parameter. In some embodiments, the at least one frequency corresponding to the at least one likely value of the cardiovascular parameter may be used to narrow the search space in the frequency domain representation of the motion sensor signal. A fundamental frequency associated with the biometric sensor signal may then be determined from one of the frequencies present in the narrowed search space of frequency domain representation of the motion sensor signal. In some embodiments, a frequency present in the frequency spectrogram of the motion sensor that is closest (by some statistical measure) to the at least one frequency corresponding to the at least one likely value of the cardiovascular parameter may be selected as the fundamental frequency associated with the biometric sensor signal. As another example, a frequency present in the frequency spectrogram of the motion sensor (and/or biometric sensor) that falls within some interval (e.g. one standard deviation) of the at least one frequency corresponding to the at least one likely value of the cardiovascular parameter may be selected as the fundamental frequency associated with the biometric sensor signal.

In some embodiments, method 700 may further comprise determining an estimated value of the cardiovascular parameter (e.g. a raw heart rate) from the fundamental frequency associated with the biometric sensor signal. In some embodiments, the estimated value of the cardiovascular parameter (e.g. a raw heart rate) may be determined based on the at least one likely value of the cardiovascular parameter (e.g. likely heart rate). As one example, a likely value of the cardiovascular parameter (e.g. likely heart rate) may be used as the estimated value of the cardiovascular parameter (e.g. a raw heart rate).

In some embodiments, method 700 may further comprise, comparing frequencies associated with the frequency domain representation of the biometric sensor signal to frequencies associated with the frequency domain representation of the motion sensor signal to determine one or more non-motion related frequencies in the frequency domain representation of the biometric sensor signal. In some embodiments, the fundamental frequency associated with the biometric sensor signal may then be determined from the one or more non-motion related frequencies in the frequency domain representation of the biometric sensor signal.

In some embodiments, the fundamental frequency associated with the biometric sensor signal may be determined by: removing frequencies associated with the frequency domain representation of the motion sensor signal from the frequency domain representation of the biometric sensor signal; and determining the fundamental frequency associated with the biometric sensor signal from frequencies remaining in the frequency domain representation of the biometric sensor signal (e.g. after removal of frequencies associated with the frequency domain representation of the motion sensor signal).

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

What is claimed is:

1. A processor-implemented method comprising:
    obtaining, with a processor, a plurality of biometric sensor signal measurements of a biometric sensor signal output by a biometric sensor, the biometric sensor signal measurements based, in part, on one or more cardiovascular parameters of a user;
    obtaining, with the processor, a plurality of motion sensor signal measurements of a motion sensor signal output by a motion sensor, the motion sensor signal measurements based, in part, on motion of the user;
    determining, with the processor, an activity type based, in part, on a comparison of a spectral power distribution corresponding to the motion sensor signal measurements with at least one threshold, wherein the at least one threshold is based on cumulative probability distributions of activity related power spectral densities;
    determining, with the processor, based on the activity type, for each cardiovascular parameter in a subset of the one or more cardiovascular parameters, a corresponding predicted cardiovascular parameter value; and
    determining, with the processor, for each cardiovascular parameter in the subset, a corresponding fundamental frequency associated with the biometric sensor signal, based, in part, on the motion sensor signal measurements and the corresponding predicted cardiovascular parameter value.

2. The method of claim 1, wherein the determination of the activity type is performed when non-motion related frequencies are not discernible in a frequency domain representation of the biometric sensor signal.

3. The method of claim 1, further comprising:
    determining, for each cardiovascular parameter in the subset, a corresponding estimated cardiovascular parameter value based, in part, on the corresponding fundamental frequency for the cardiovascular parameter.

4. The method of claim 1, further comprising determining the spectral power distribution in the motion sensor signal comprising:
    obtaining a spectral power value based, in part, on a first set of harmonics in a frequency domain representation of the motion sensor signal.

5. The method of claim 4, wherein obtaining the spectral power value comprises:
    determining a plurality of second sets of harmonics in the frequency domain representation of the motion sensor signal;
    obtaining, corresponding to each second set of harmonics, a corresponding power measure;
    comparing the corresponding power measures for the plurality of second sets of harmonics; and
    selecting, based on the comparison, the first set of harmonics from the plurality of second sets of harmonics.

6. The method of claim 5, wherein selecting the first set of harmonics from the plurality of second sets of harmonics comprises:
    selecting, as the first set of harmonics, a second set of harmonics with a highest power measure relative to other second sets of harmonics in the plurality of second sets of harmonics.

7. The method of claim 5, wherein obtaining the corresponding power measure for each second set of harmonics comprises at least one of:
    obtaining the corresponding power measure based on a corresponding count of a number of spectral peaks in the second set of harmonics; or
    obtaining the corresponding power measure based on a corresponding sum of amplitudes of spectral peaks in the second set of harmonics; or
    obtaining the corresponding power measure based on a corresponding sum of integrated spectral peak signals in the second set of harmonics.

8. The method of claim 5, wherein comparing the corresponding power measures for the plurality of second sets of harmonics comprises one of:
    comparing the corresponding power measures for the plurality of second sets of harmonics to each other; or
    comparing the corresponding power measures for the plurality of second sets of harmonics to the at least one threshold.

9. The method of claim 1, wherein determining the activity type associated with the motion of the user comprises:
    detecting a motion pattern based, in part, on the motion sensor signal measurements; and
    determining the activity type based on the detected motion pattern.

10. The method of claim 1, wherein the one or more cardiovascular parameters comprise a heart rate and the corresponding predicted cardiovascular parameter value comprises a predicted heart rate.

11. The method of claim 1, wherein determining the corresponding predicted cardiovascular parameter value for each cardiovascular parameter in the subset comprises:
    determining the corresponding predicted cardiovascular parameter value for each cardiovascular parameter in the subset using a physiological model, wherein, for each cardiovascular parameter in the subset, the physiological model correlates the activity type with the corresponding predicted cardiovascular parameter value.

12. The method of claim 11, wherein the correlation of the activity type with the corresponding predicted cardiovascular parameter value is user-specific.

13. A device comprising:
a motion sensor, the motion sensor to output a motion sensor signal based, in part, on motion of a user,
a biometric sensor, the biometric sensor to output a biometric sensor signal based, in part, on one or more cardiovascular parameters of the user, and
a processor coupled to the motion sensor and the biometric sensor, wherein the processor is configured to:
obtain a plurality of biometric sensor signal measurements of the biometric sensor signal;
obtain a plurality of motion sensor signal measurements of the motion sensor signal;
determine an activity type based, in part, on a comparison of a spectral power distribution corresponding to the motion sensor signal measurements with at least one threshold, wherein the at least one threshold is based on cumulative probability distributions of activity related power spectral densities;
determine, based on the activity type, for each cardiovascular parameter in a subset of the one or more cardiovascular parameters, a corresponding predicted cardiovascular parameter value; and
determine, for each cardiovascular parameter in the subset, a corresponding fundamental frequency associated with the biometric sensor signal, based, in part, on the motion sensor signal measurements and the corresponding predicted cardiovascular parameter value.

14. The device of claim 13, wherein the processor is configured to perform the determination of the activity type when non-motion related frequencies are not discernible in a frequency domain representation of the biometric sensor signal.

15. The device of claim 13, wherein the processor is further configured to:
determine, for each cardiovascular parameter in the subset, a corresponding estimated cardiovascular parameter value based, in part, on the corresponding fundamental frequency for the cardiovascular parameter.

16. The device of claim 13, wherein the processor is configured to determine the spectral power in the motion sensor signal by being configured to:
obtain a spectral power value based, in part, on a first set of harmonics in a frequency domain representation of the motion sensor signal; and
determine the activity type based on the spectral power value.

17. The device of claim 16, wherein to obtain the spectral power value, the processor is configured to:
determine a plurality of second sets of harmonics in the frequency domain representation of the motion sensor signal;
obtain, corresponding to each second set of harmonics, a corresponding power measure;
compare the corresponding power measures for the plurality of second sets of harmonics; and
select, based on the comparison, the first set of harmonics from the plurality of second sets of harmonics.

18. The device of claim 17, wherein to select the first set of harmonics from the plurality of second sets of harmonics, the processor is configured to:
select, as the first set of harmonics, a second set of harmonics with a highest power measure relative to other second sets of harmonics in the plurality of second sets of harmonics.

19. The device of claim 17, wherein to obtain the corresponding power measure for each second set of harmonics, the processor is configured to perform at least one of:
obtain the corresponding power measure based on a corresponding count of a number of spectral peaks in the second set of harmonics; or
obtain the corresponding power measure based on a corresponding sum of amplitudes of spectral peaks in the second set of harmonics; or
obtain the corresponding power measure based on a corresponding sum of integrated spectral peak signals in the second set of harmonics.

20. The device of claim 17, wherein to compare the corresponding power measures for the plurality of second sets of harmonics, the processor is configured to perform one of:
compare the corresponding power measures for the plurality of second sets of harmonics to each other; or
compare the corresponding power measures for the plurality of second sets of harmonics to the at least one threshold.

21. The device of claim 13, wherein to determine the activity type associated with the motion of the user, the processor is configured to:
detect a motion pattern based, in part, on the motion sensor signal measurements; and
determine the activity type based on the detected motion pattern.

22. The device of claim 13, wherein the one or more cardiovascular parameters comprise a heart rate and the corresponding predicted cardiovascular parameter value comprises a predicted heart rate.

23. A device comprising:
means for obtaining a plurality of biometric sensor signal measurements of an biometric sensor signal, the biometric sensor signal measurements based, in part, on one or more cardiovascular parameters of a user;
means for obtaining a plurality of motion sensor signal measurements of a motion sensor signal, the motion sensor signal measurements based, in part, on motion of the user;
means for determining an activity type based, in part, on a comparison of a spectral power distribution corresponding to the motion sensor signal measurements with at least one threshold, wherein the at least one threshold is based on cumulative probability distributions of activity related power spectral densities;
means for determining, based on the activity type, for each cardiovascular parameter in a subset of the one or more cardiovascular parameters, a corresponding predicted cardiovascular parameter value; and
means for determining, for each cardiovascular parameter in the subset, a corresponding fundamental frequency associated with the biometric sensor signal, based, in part, on the motion sensor signal measurements and the corresponding predicted cardiovascular parameter value.

24. The device of claim 23, wherein the determination of the activity type is performed when non-motion related frequencies are not discernible in a frequency domain representation of the biometric sensor signal.

25. The device of claim 23, further comprising:
determining, for each cardiovascular parameter in the subset, a corresponding estimated cardiovascular parameter value based, in part, on the corresponding fundamental frequency for the cardiovascular parameter.

26. A non-transitory computer-readable medium comprising executable instructions to configure a processor to:

obtain, with the processor, a plurality of biometric sensor signal measurements of a biometric sensor signal output by a biometric sensor, the biometric sensor signal measurements based, in part, on one or more cardiovascular parameters of a user;

obtain, with the processor, a plurality of motion sensor signal measurements of a motion sensor signal output by a motion sensor, the motion sensor signal measurements based, in part, on motion of the user;

determine, with the processor, an activity type based, in part, on a comparison of a spectral power distribution corresponding to the motion sensor signal measurements with at least one threshold, wherein the at least one threshold is based on cumulative probability distributions of activity related power spectral densities;

determine, with the processor, based on the activity type, for each cardiovascular parameter in a subset of the one or more cardiovascular parameters, a corresponding predicted cardiovascular parameter value; and determine, with the processor, for each cardiovascular parameter in the subset, a corresponding fundamental frequency associated with the biometric sensor signal, based, in part, on the motion sensor signal measurements and the corresponding predicted cardiovascular parameter value.

27. The computer-readable medium of claim 26, wherein the determination of the activity type is performed when non-motion related frequencies are not discernible in a frequency domain representation of the biometric sensor signal.

28. The computer-readable medium of claim 26, wherein the executable instructions further comprise:

determine, for each cardiovascular parameter in the subset, a corresponding estimated cardiovascular parameter value based, in part, on the corresponding fundamental frequency for the cardiovascular parameter.

* * * * *